US012575496B2

(12) United States Patent
Somarowthu et al.

(10) Patent No.: US 12,575,496 B2
(45) Date of Patent: Mar. 17, 2026

(54) SYSTEM AND METHOD FOR TERAHERTZ FREQUENCY CROP CONTAMINATION DETECTION AND HANDLING

(71) Applicant: Deere & Company, Moline, IL (US)

(72) Inventors: Mahesh Somarowthu, Pune (IN); Noel W. Anderson, Fargo, ND (US)

(73) Assignee: DEERE & COMPANY, Moline, IL (US)

( * ) Notice: Subject to any disclaimer, the term of this patent is extended or adjusted under 35 U.S.C. 154(b) by 320 days.

(21) Appl. No.: 17/903,230

(22) Filed: Sep. 6, 2022

(65) Prior Publication Data

US 2022/0408643 A1     Dec. 29, 2022

Related U.S. Application Data

(63) Continuation-in-part of application No. 16/601,219, filed on Oct. 14, 2019, now Pat. No. 11,696,529.

(51) Int. Cl.
*A01D 41/127*      (2006.01)
*G01N 21/3563*     (2014.01)
(Continued)

(52) U.S. Cl.
CPC ..... *A01D 41/1277* (2013.01); *G01N 21/3563* (2013.01); *G01N 21/3581* (2013.01); *G01N 33/0098* (2013.01)

(58) Field of Classification Search
None
See application file for complete search history.

(56) References Cited

U.S. PATENT DOCUMENTS

| | | | |
|---|---|---|---|
| 5,315,243 A | 5/1994 | Kempster et al. | |
| 5,708,366 A | 1/1998 | Nelson | |

(Continued)

FOREIGN PATENT DOCUMENTS

| | | |
|---|---|---|
| CN | 1748451 A | 3/2006 |
| CN | 108267418 A | 7/2018 |

(Continued)

OTHER PUBLICATIONS

Phys-Org, "Designing Sensors to Detect Foreign Bodies in Food", https://phys.org/news/2017-03-sensors-foreign-bodies-food.html, Mar. 31, 2017. (03 pages).

(Continued)

*Primary Examiner* — Mark A Shabman
(74) *Attorney, Agent, or Firm* — Christopher J. Volkmann; KELLY, HOLT & CHRISTENSON PLLC

(57)     ABSTRACT

A terahertz frequency-based sensing system for an agricultural harvester is provided. The system includes a terahertz sensor mounted to the agricultural harvester. The terahertz sensor at least one a terahertz source disposed to direct electromagnetic radiation toward a harvest material of the agricultural harvester. At least one terahertz detector is disposed to detect the terahertz electromagnetic radiation after the terahertz electromagnetic radiation interacts with the harvest material. A controller is operably coupled to the at least one terahertz detector and is configured to detect at least one harvest-related parameter based on a signal from the at least one terahertz detector and to perform an action based on the at least one detected parameter.

20 Claims, 9 Drawing Sheets

(51) Int. Cl.
  *G01N 21/3581*    (2014.01)
  *G01N 33/00*    (2006.01)

(56)        References Cited

U.S. PATENT DOCUMENTS

| | | | |
|---|---|---|---|
| 5,871,397 | A | 2/1999 | Nelson et al. |
| 5,934,997 | A | 8/1999 | Nelson et al. |
| 5,939,888 | A | 8/1999 | Nelson |
| 5,970,800 | A | 10/1999 | Gunneskov et al. |
| 6,119,442 | A * | 9/2000 | Hale .................... A01D 41/127 |
| | | | 56/10.2 H |
| 6,147,502 | A | 11/2000 | Fryer et al. |
| 6,430,903 | B1 | 8/2002 | Christiansen |
| 6,526,120 | B1 | 2/2003 | Gray et al. |
| 6,606,571 | B2 | 8/2003 | Phelan et al. |
| 6,637,179 | B2 | 10/2003 | Duncan |
| 9,410,840 | B2 | 8/2016 | Acheson et al. |
| 9,631,964 | B2 | 4/2017 | Gelinske et al. |
| 9,857,297 | B2 | 1/2018 | Hilscher et al. |
| 10,260,931 | B2 | 4/2019 | Acheson et al. |
| 10,371,558 | B2 | 8/2019 | Tevs et al. |
| 10,481,105 | B2 | 11/2019 | Advani et al. |
| 10,524,409 | B2 | 1/2020 | Posselius et al. |
| 10,660,268 | B2 | 5/2020 | Dybro et al. |
| 10,871,458 | B2 | 12/2020 | Todd et al. |
| 11,140,809 | B2 | 10/2021 | Barychev et al. |
| 11,256,899 | B2 | 2/2022 | Barychev et al. |
| 11,770,265 | B2 | 9/2023 | Haidous et al. |
| 2016/0000008 | A1 | 1/2016 | Scholer et al. |
| 2016/0078611 | A1 | 3/2016 | Butts et al. |
| 2016/0084813 | A1 | 3/2016 | Anderson et al. |
| 2016/0084987 | A1 | 3/2016 | Dybro et al. |
| 2016/0174456 | A1* | 6/2016 | Barychev ................. A01C 1/02 |
| | | | 47/14 |
| 2016/0282171 | A1 | 9/2016 | Acheson et al. |
| 2017/0023469 | A1 | 1/2017 | Zimdars et al. |
| 2017/0082540 | A1* | 3/2017 | Seo .................... G01N 21/3581 |
| 2017/0287303 | A1 | 10/2017 | Lang et al. |
| 2018/0042174 | A1* | 2/2018 | Li ........................... G06F 17/18 |
| 2018/0059034 | A1* | 3/2018 | Advani ...................... G01F 1/74 |
| 2018/0260674 | A1 | 9/2018 | Hamilton et al. |
| 2018/0310474 | A1* | 11/2018 | Posselius ............. A01D 41/127 |
| 2019/0133037 | A1 | 5/2019 | Todd et al. |
| 2019/0137416 | A1 | 5/2019 | Todd et al. |
| 2019/0183047 | A1 | 6/2019 | Dybro et al. |
| 2019/0236332 | A1 | 8/2019 | Barychev et al. |
| 2021/0105941 | A1 | 4/2021 | Yu et al. |
| 2021/0127558 | A1 | 5/2021 | Hubner et al. |
| 2021/0243950 | A1 | 8/2021 | Blank et al. |
| 2021/0344516 | A1 | 11/2021 | Haidous et al. |
| 2022/0039310 | A1 | 2/2022 | Johnson et al. |

FOREIGN PATENT DOCUMENTS

| | | |
|---|---|---|
| CN | 108279261 A | 7/2018 |
| CN | 109187417 A | 1/2019 |
| CN | 112858215 A | 5/2021 |
| CN | 113189611 A | 7/2021 |
| CN | 113218908 A | 8/2021 |
| DE | 3511355 C2 | 10/1985 |
| DE | 19648126 B4 | 1/2009 |
| EP | 0840109 A2 | 5/1998 |
| EP | 0843959 A1 | 5/1998 |
| EP | 0940656 A1 | 9/1999 |
| EP | 3837959 A1 | 6/2021 |

OTHER PUBLICATIONS

Terasense Group, "Terahertz Food Inspection and Quality Control" I TeraSense, https://terasense.com/ applications/terahertz-food-inspection/, 2008-2022, (13 pages).

Ontario, "Common Weeds Poisonous to Grazing Livestock", https://www.ontario.ca/page/common-weeds-poisonous-grazing-livestock, Jul. 20, 2022. (09 pages).

Utah State University Extension, "Toxic Contaminants in Harvested Forages", Clell V. Bagley, DVM, Animal Health Fact Sheet, Jul. 1997, (4 pages).

PMG Engineering, "Metal Contamination in Food Industry—Detection & Reduction", Sep. 18, 2020. (10 pages).

Scientific Reports, "Terahertz and Infrared Characteristic Absorption Spectra of Aqueous Glucose and Fructose Solutions", Chao Song et al., DOI:10.1038/s41598-018-27310-7, www.nature.com/ scientificreports, Jun. 12, 2018. (8 pages).

MDPI-Toxins, "Mycotoxin Contamination in Sugarcane Grass and Juice: First Report on Detection of Multiple Mycotoxins and Exposure Assessment for Aflatoxins B1 and G1 in Humans", Mohamed F. Abdallah et al., http://www. mdpi.com/journal/toxins, Nov. 18, 2016. (12 pages).

Liu, J. et al. "Detection of Genetically Modified Sugarcane By Using Terahertz Spectroscopy and Chemometrics", Journal of Applied Spectroscopy, vol. 85, No. 1, p. 119, Gale Academic OneFile, http://dx.doi.org/10.1007/s 10812-018-0621-9, Mar. 2018. (11 pages).

Zhang, H. et al., Abstract for "Detection of Poisonous Herbs by Terahertz Time-Domain Spectroscopy", Journal of Applied Spectroscopy, vol. 85, Issue 1, pp. 197-202, Mar. 2018. (1 page).

Research Gate, Abstract for "Toxic Chemical Compound Detection by Terahertz Spectroscopy", Liu Yang, Reviews in Analytical Chemistry, https://www.researchgate.net/publication/325751558, Jun. 2018. (1 page).

Office Action for U.S. Appl. No. 16/601,219, dated Aug. 16, 2022, 10 pages.

Kormann et al. (1998). Testing stand for yield measurement systems in combine harvesters. In ASAE International Conference. Paper No. 983102, Jul. 1998, 10 pages.

Nelson et al., Microwave Sensing of Moisture Content and Bulk Density in Flowing Grain and Seed, American Society of Agricultural and Biological Engineers, ASABE 59(2): 429-433. (doi: 10.13031/trans.59.11377) @2016, 2 pages.

Chung et al. (2016). Sensing technologies for grain crop yield monitoring systems: A review. Journal of Biosystems Engineering, 41(4), 408-417, 10 pages.

Noh, B. B. M. (2010). Application of microwave sensors to potato products. The University of Manchester (United Kingdom). 161 pages.

Application and Drawings for U.S. Appl. No. 17/903,231, filed Sep. 6, 2022, 41 pages,.

Notice of Allowance for U.S. Appl. No. 16/601,219, dated Dec. 20, 2022, 8 pages.

Office Action for U.S. Appl. No. 17/903,231, dated Feb. 27, 2025, 20 pages.

Office Action for U.S. Appl. No. 18/191,199, dated Mar. 13, 2025, 13 pages.

Afsah-Hejri, Leili, et al. "Terahertz spectroscopy and imaging: A review on agricultural applications." Computers and Electronics in Agriculture 177 (2020): 105628, 24 pages.

"Metal Contamination in Food Industry-Detection & Reduction" retrieved at https://www.pmg.engineering/metal-contamination-in-food-industry-detection-reduction, dated Sep. 18, 2020, 12 pages.

McIntosh, Alexander I., et al. "Terahertz spectroscopy: a powerful new tool for the chemical sciences?." Chemical Society Reviews 41.6 (2012): 2072-2082, 11 pages.

Edgar, Matthew P., Graham M. Gibson, and Miles J. Padgett. "Principles and prospects for single-pixel imaging." Nature photonics 13.1 (2019): 13-20, 14 pages.

Hillger, Philipp, et al. "Terahertz imaging and sensing applications with silicon-based technologies." IEEE Transactions on Terahertz Science and Technology 9.1 (2018): 1-19, 19 pages.

Blanchard, François, et al. "A low-cost terahertz camera." Applied Sciences 9,12 (2019): 2531, 8 pages.

T. Gua et al., "Evaluation of wheat seeds by terahertz imaging," 2013 6th UK, Europe, China Millimeter Waves and THz Technology Workshop (UCMMT), 2013, pp. 1-2. doi: 10.1109/UCMMT. 2013.6641513, 2 pages.

R. Gente et al., "Quality Control of Sugar Beet Seeds With THz Time-Domain Spectroscopy," in IEEE Transactions on Terahertz Science and Technology, vol. 6, No. 5, pp. 754-756, Sep. 2016, doi: 10.1109/TTHZ.2016.2593985, 3 pages.

(56)          References Cited

OTHER PUBLICATIONS

Stantchev, Rayko Ivanov, et al. "Real-time terahertz imaging with a single-pixel detector." Nature communications 11.1 (2020): 1-8, 8 pages.

Shen, Yin, et al. "Detection of impurities in wheat using terahertz spectral imaging and convolutional neural networks." Computers and Electronics in Agriculture 181 (2021): 105931, 8 pages.

Zang, Ziyi, et al. "Terahertz spectral imaging based quantitative determination of spatial distribution of plant leaf constituents," Plant Methods 15.1 (2019): 1-11, 11 pages.

Liu, Wei et al. "Discrimination of transgenic soybean seeds by terahertz spectroscopy." Scientific reports vol. 6:35799. Oct. 26, 2016, doi: 10.1038/srep35799, 7 pages.

Qin, Binyi, et al. "Identification of genetically modified cotton seeds by terahertz spectroscopy with MPGA-SVM." Optik 142 (2017): 576-582, 7 pages.

Pan, Shubao, et al. "An Unsupervised Learning Method for the Detection of Genetically Modified Crops Based on Terahertz Spectral Data Analysis." Security and Communication Networks 2021 (2021), 7 pages.

Shenzhen Institute of Terahertz Technology and Innovation, Terahertz Infrared Food, Drug, Drug Detector, http://www.szthz.org/index. php/Achievement-index-id-19.html?l=e, 6 pages, Retrieved on Aug. 29, 2022.

Terahertz Solutions for Science and Industry, Cameras, Scanners, Detectors, and Sources, 12 pages, Retrieved Aug. 29, 2022.

Chen T., et al., "Discrimination of GMOs Using Terahertz Spectroscopy and CS-SVM," PubMed, Feb. 2017, vol. 37, No. 2, pp. 618-623 (1 Page), Abstract, [Retrieved on Sep. 19, 2024] Retrieved from URL: https://pubmed.ncbi.nlm.nih.gov/30292182/.

Non-Final Office Action for U.S. Appl. No. 17/903,231, dated Aug. 20, 2024, 12 Pages.

Search Report for German Application No. 102023120643.5, dated Dec. 21, 2023, 4 Pages.

Yang L., et al., "Toxic Chemical Compound Detection by Terahertz Spectroscopy," Reviews in Analytical Chemistry, Research Gate, 2018, 10 Pages, Received on Sep. 22, 2017, Retrieved from URL: https://www.researchgate.net/publication/325751558_Toxic_chemical_compound_detection_by_terahertz_spectroscopy_A_review.

Zhang H., et al., "Detection of Poisonous Herbs by Terahertz Time-Domain Spectroscopy," Journal of Applied Spectroscopy, Mar. 2018, vol. 85, Issue No. 1, pp. 197-202, Retrieved from URL: https://www.researchgate.net/publication/324214203_Detection_of_Poisonous_Herbs_by_Teraheriz_Time-Domain_Spectroscopy.

\* cited by examiner

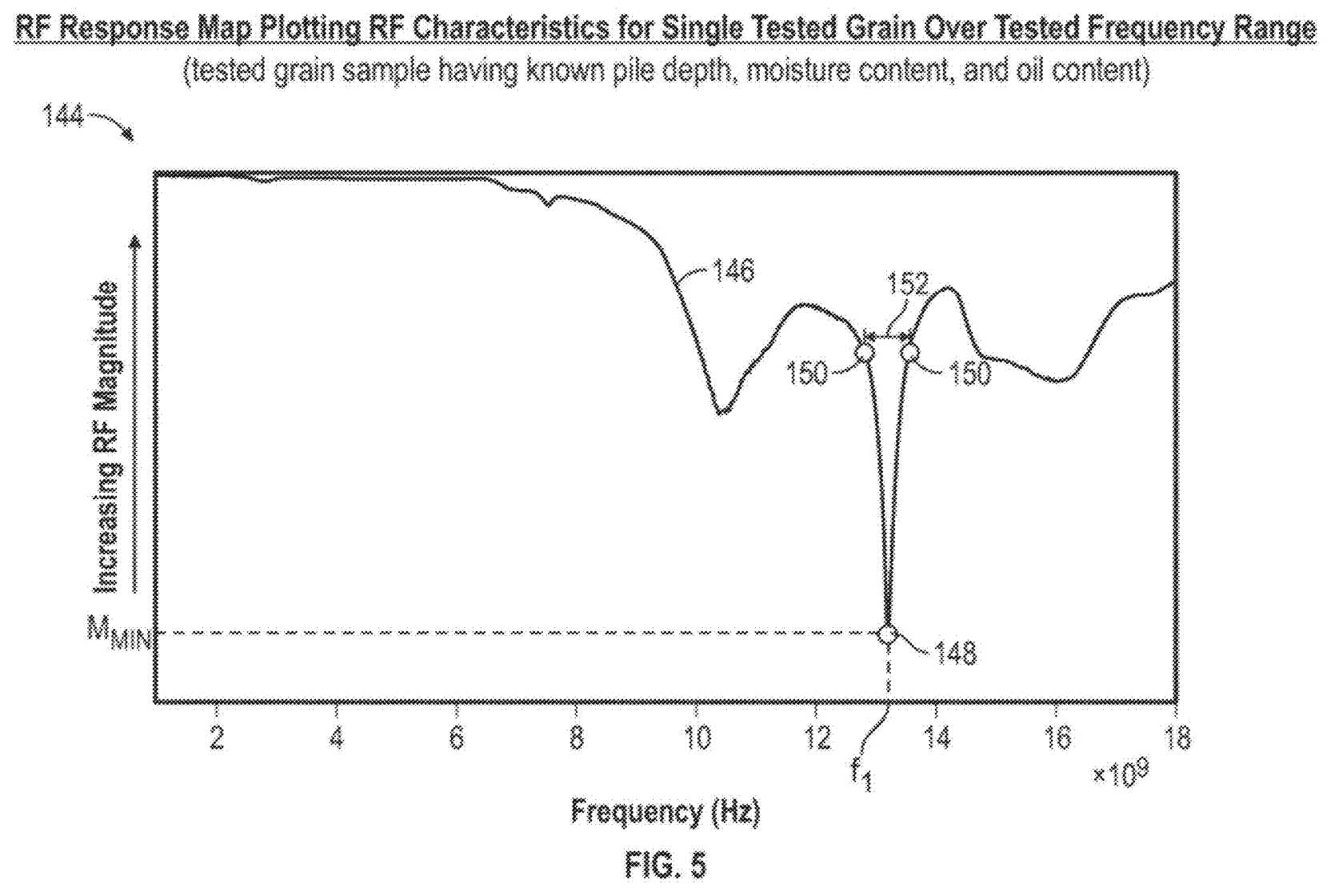

RF Response Map Plotting RF Characteristics for Single Tested Grain Over Tested Frequency Range
(tested grain sample having known pile depth, moisture content, and oil content)

FIG. 5

Frequency (Hz)

Increasing RF Magnitude

SYSTEM AND METHOD FOR TERAHERTZ FREQUENCY CROP CONTAMINATION DETECTION AND HANDLING

CROSS-REFERENCE TO RELATED APPLICATIONS

The present application is based on and claims the benefit of U.S. patent application Ser. No. 16/601,219 filed on Oct. 14, 2019, the content of which application is hereby incorporated by reference in its entirety.

FIELD OF THE DESCRIPTION

This disclosure relates to Terahertz-frequency based detection systems for crop contamination detection and handling.

BACKGROUND

There are a wide variety of different types of agricultural machines. Some agricultural machines include harvesters, such as combine harvesters, sugar cane harvesters, cotton harvesters, self-propelled forage harvesters, and windrowers. Some harvesters can also be fitted with different types of headers to harvest different types of crops.

Combine harvesters (also referred to as "agricultural combines") have greatly improved the efficiency with which corn, canola, soybeans, wheat, oats, sunflowers, and other crops are harvested, threshed, cleaned, and collected for distribution to consumers. Generally, combine harvesters are relatively complex, self-propelled machines capable of harvesting large swathes of crop plants as the harvester travels over a crop field, while separating grain from material other than grain (MOG) within the harvester. After cleaning, the harvested grain is delivered into a grain storage tank, typically by conveyance through a clean grain elevator. As combine harvesters become increasingly advanced, sensor subsystems are now integrated into harvesters to measure the characteristics related to the crop and/or non-crop materials.

The discussion above is merely provided for general background information and is not intended to be used as an aid in determining the scope of the claimed subject matter.

SUMMARY

A terahertz frequency-based sensing system for an agricultural harvester is provided. The system includes a terahertz sensor mounted to the agricultural harvester. The terahertz sensor at least one a terahertz source disposed to direct electromagnetic radiation toward a harvest material of the agricultural harvester. At least one terahertz detector is disposed to detect the terahertz electromagnetic radiation after the terahertz electromagnetic radiation interacts with the harvest material. A controller is operably coupled to the at least one terahertz detector and is configured to detect at least one harvest-related parameter based on a signal from the at least one terahertz detector and to perform an action based on the at least one detected parameter.

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 5 graphically illustrates an RF sensor reading (here, measured in terms of wave amplitude or magnitude) of a tested grain sample over a predetermined frequency range, which may further be utilized by the controller in determining grain mass and a first constituent content of a harvested grain in embodiments.

Figure 1:
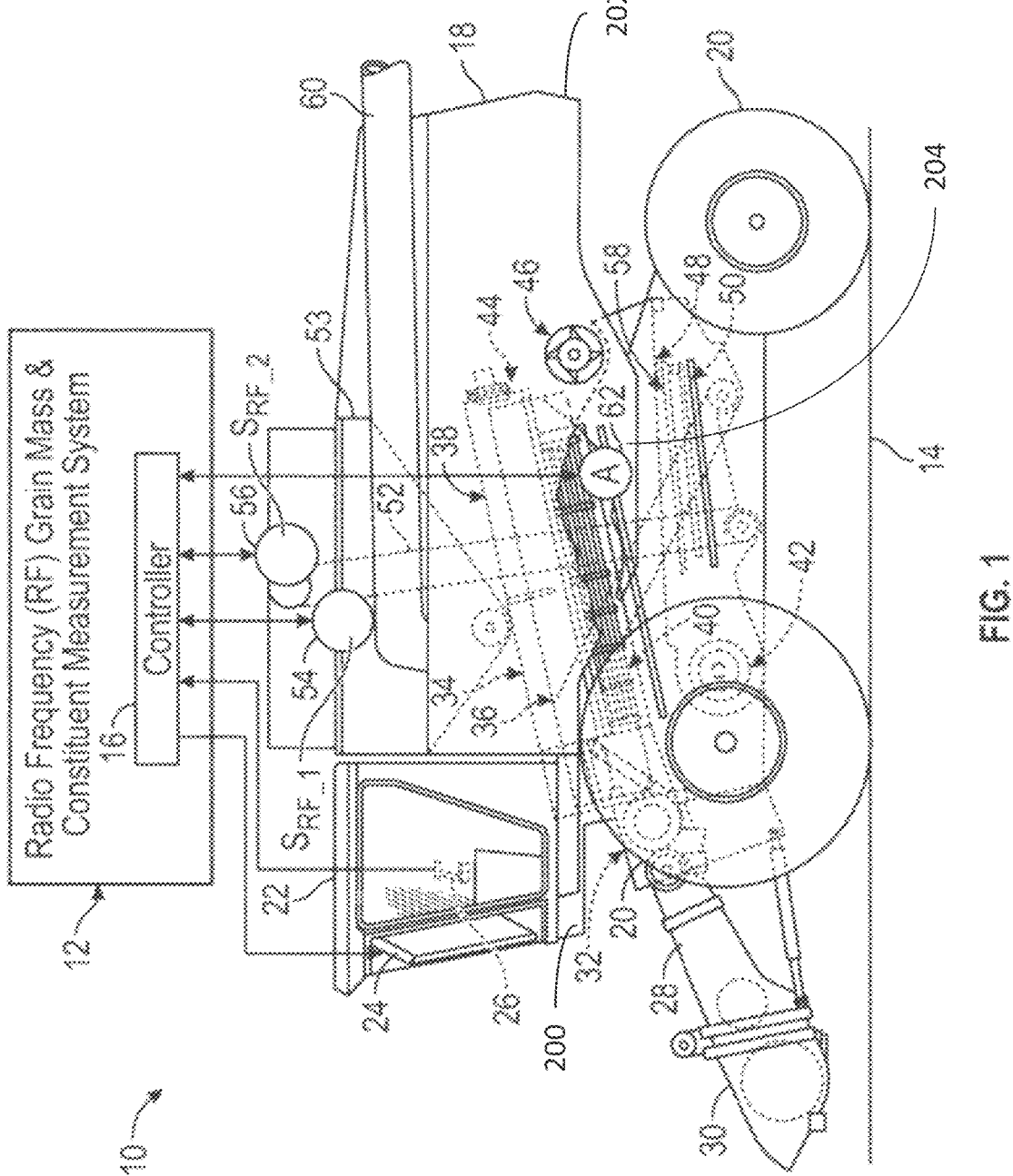
FIG. 1 is a schematic of a combine harvester equipped with the radio frequency (RF) grain and mass constituent measurement system, as illustrated in accordance with an example embodiment.

Like reference symbols in the various drawings indicate like elements. For simplicity and clarity of illustration, descriptions and details of well-known features and techniques may be omitted to avoid unnecessarily obscuring the example and non-limiting embodiments of the invention described in the subsequent Detailed Description. It should further be understood that features or elements appearing in the accompanying figures are not necessarily drawn to scale unless otherwise stated.

DETAILED DESCRIPTION

For the purposes of promoting an understanding of the principles of the present disclosure, reference will now be made to the examples illustrated in the drawings, and specific language will be used to describe the same. It will nevertheless be understood that no limitation of the scope of the disclosure is intended. Any alterations and further modifications to the described devices, instruments system, methods, and any further application of the principles of the present disclosure are fully contemplated as would normally occur to one skilled in the art to which the disclosure relates. In particular, it is fully contemplated that the features, components, steps, or a combination thereof described with respect to one example may be combined with the features, components, steps, or a combination thereof described with respect to other examples of the present disclosure.

The International Telecommunications Union (ITU) defines Terahertz electromagnetic radiation as having a frequency between 0.3 and 3 Terahertz. Other sources define the band to include frequencies as low as 0.1 Terahertz and as high as 30 Terahertz. As used herein, the band includes frequencies from 0.1 Terahertz to 30 Terahertz. Terahertz radiation is subject to significant laboratory research and shows promise for agricultural applications. It lies between microwave and infrared on the electromagnetic spectrum and provides the advantage of at least partial penetration into objects, but is not considered ionizing radiation, like X-rays. As such, Terahertz radiation does not trigger a requirement for a safety officer, nor is it subject to significant regulations, such as those that apply to X-rays. However, Terahertz electromagnetic radiation does provide improved detection abilities over optical techniques, IR and UV. In accordance with embodiments described below, Terahertz electromagnetic radiation is employed relative to the harvesting operation to better detect and react to non-ferrous foreign materials. Terahertz electromagnetic radiation is also used to detect contaminants such as GMOs, soil/ash, chemical residues (e.g., pesticides), and biotoxins, such as aflatoxin.

Modern combine harvesters are equipped with sensor subsystems for measuring grain mass and moisture content of harvested grains. In one common approach, grain mass is determined by detecting the force at which harvested grain strikes a surface positioned within the outlet end of the clean grain elevator. More specifically, the strike force of the clean grain may be measured utilizing a load cell, which is positioned behind an impact plate struck by the clean grain when flung or thrown from the rotating paddles of the grain elevator. As the grain strikes the impact plate before falling into the clean grain tank, the load cell detects the force at which the grain strikes the impact plate. This strike force, taken in conjunction with the grain elevator speed, is then utilized to solve for grain mass. Once determined, grain mass can then be utilized to in grain mass flow rate and grain yield calculations, along with other known parameters, such as header width and harvester speed.

In addition to grain mass, grain moisture content is also desirably tracked by combine harvesters. The moisture content of a harvested grain impacts the propensity of the grain to spoil, shrink, or become damaged during processing and storage. Additionally, variations in grain moisture content can affect the accuracy of the above-described grain mass measurements and are thus desirably compensated for when calculating grain mass. For these reasons, combine harvesters are also commonly equipped with sensors for estimating the moisture content of harvested grain. In many instances, grain moisture content is estimated by measuring capacitance across a known volume of grain, which is diverted into a test channel or "bypass" from the clean grain stream. The dimensions of the bypass determine the sampled grain volume, and electrodes (e.g., metal plates) border the sides of the bypass to enable an electrical current to be passed through the sampled grain volume to measure capacitance. The capacitance measurement is then converted to a moisture content estimate utilizing a pre-established correlation or equation, noting that electrical conductivity tends to increase (and thus capacitance tends to decrease) as the moisture content of the grain increases. The capacitance estimate may then be considered by the processing architecture or "controller" of the combine harvester to more accurately assess grain mass. In other instances, the sampled grain volume may be weighed, and the weight may be utilized to estimate grain moisture content (or grain mass) in addition to or in lieu of a capacitance measurement. After estimating grain moisture in this manner, the sampled grain volume may then be returned to the clean grain stream, and such process steps may be repeated to estimate grain moisture content on an iterative basis.

While useful in a general sense, the above-described techniques for measuring grain mass and moisture content remain limited in multiple respects. Such measurement techniques can be somewhat inaccurate, overly complex, and require repeated calibration. Consider, for example, the above-described technique for estimating the moisture content of a grain processed by a combine harvester. The need to repeatedly divert or sequester fractions of the newly-harvested grain from the clean grain stream into a dedicate bypass, measure the capacitance (or weight) of the sampled grain, and then return the sampled grain to the clean grain stream is a cumbersome process, which adds undesired cost and complexity to the combine harvester. Further, by the nature of such a quasi-random sampling process, the grain moisture estimates are taken at discrete points in time, while interrupting flow of the clean grain stream to a limited extent. In certain instances, the grain moisture estimates may be temporary offset from the strike force measurements by a significant time delay, exacerbating inaccuracies in estimating grain mass under changing grain conditions.

In view of such deficiencies, various alternative techniques for measuring grain mass and moisture content have been suggested and, in certain instances, implemented. Such alternative techniques are, however, also associated with various shortcomings. As a specific example, it has been suggested that grain mass may be measured by impinging harvested grain with high energy, ionizing radiation in the form of x-rays or gamma rays. Such an approach may permit determination of grain mass and/or moisture content by measuring the degree to which the high energy, ionizing electromagnetic (EM) radiation is absorbed into the harvested grain. This notwithstanding, proposed systems incorporating high energy emitter and receiver antennae tend to add considerable cost and complexity to the sensor subsystem and may be subject to various governmental regulations. Further, as do more conventional techniques of the type described above, such alternative techniques for measuring grain mass and moisture content remain limited in another significant respect, as well—such measurement techniques provide little, if any additional useful information pertaining to the composition of a harvested grain beyond the moisture content estimate itself.

To overcome the above-noted deficiencies associated with such conventional grain mass measurement systems, the following discloses radio frequency-based grain mass and constituent measurement systems well suited for usage within combine harvesters. As indicated by the term "radio-frequency based," the below-described measurement systems utilize radio frequency (RF) measurements to measure or estimate the grain mass and constituent content(s) of a currently-harvested grain; that is, a grain extracted from crop plants ingested and then processed by a combine harvester equipped with the measurement system. For ease of reference, the RF-based grain mass and constituent measurement systems are alternatively referred hereafter to as "RF grain mass and constituent measurement systems." Such terminology denotes that RF grain mass and constituent measurement system utilizes RF signals in assessing grain mass and the constituent content level(s), but does not preclude the possibility that the measurement system may (and often will) utilize other non-RF input data in rendering such assessments. Further, the term "constituent content" refers to the degree or level to which the grain contains at least one constituent, whether moisture or a non-moisture constituent. Examples of non-moisture constituents include protein, cellulose, starch, or oil contained in the grain. Such constituent content levels or quantities will often be expressed as a volume or weight percentage, such as a protein, cellulose, starch, or oil percentage (%) by weight; however, other manners in expressing the fractional quantity of a particular constituent within the grain are equally viable.

As indicated above, embodiments of the RF grain mass and constituent measurement system may also consider non-RF sensor input and other non-RF input data in determining grain mass, moisture content, non-moisture constituent measurement(s), and other grain-related parameters, such as a grain mass flow rate or overall grain yield. The measurement system may recall from memory and apply pre-established conversion factors and equations where appropriate; e.g., as utilized in, for example, converting a measured grain volume (inferred from the below-described RF response signals) to grain mass. Clean grain elevator speed, or a similar parameter, may be considered when further converting grain mass to grain mass flow rate through the combine harvester. Operator input data may also be considered when pertinent, with such operator input potentially specifying a particular crop type or crop category currently processed by the combine harvester in embodiments.

The RF grain mass and constituent measurement systems can include any practical number of RF sensors (emitters, receivers, and other associated hardware), which collectively form an RF sensor subsystem. In certain embodiments, the RF sensor subsystem can include a single RF receiver and emitter pair, which cycles through multiple fixed frequencies during operation; or, instead, which modulates the emitted RF energy over a predetermined frequency range. In other instances, the RF sensor subsystem may contain two or more RF sensors, with each RF sensor operating at a unique frequency or frequency range within the RF domain. When including two or more RF sensors, the sensor subsystem can utilize real-time data to resolve multiple parameters pertaining to the harvested grain, while permitting continual, uninterrupted flow of the clean grain stream. Further, each RF sensor may be optimized to operate at a unique frequency or frequency range and tailored to maximize signal-to-noise ratio within its local structural environment; e.g., by customizing antenna shape and dimensions to best suit the region of the combine harvester into which the RF sensor is integrated. Each RF sensor is beneficially optimized to provide a sensor field-of-view (FOV) or interrogation area through which substantially all grain contained in the clean grain stream passes, while further minimizing structural interference from any RF-interactive (e.g., metal) components within the interrogation area.

In various implementations in which the sensor subsystem includes at least first and second RF sensors, a first RF sensor is positioned to capture RF sensor readings of the grain within the clean grain stream at a location in which the grain is relatively compact or aggregated into a consolidated mass; e.g., as when the grain is distributed into discrete piles supported by the paddles of the clean grain elevator. Additionally, in such implementations, the second RF sensor may be positioned to capture RF sensor readings of the clean grain when in a more dispersed distribution, as when airborne and discharged from the paddles through the outlet of the clean grain elevator. In this case, the second RF sensor may be imparted with a more expansive FOV or interrogation area than is the first RF sensor to ensure the substantial entirety of the grain discharged through outlet of the clean grain elevator is impinged by RF energy and captured by the corresponding RF sensor readings.

The frequencies at which the sensor or sensors within the RF sensor subsystem operate will vary between embodiments. The operational frequencies of the RF sensors can be tailored to best suit a particular sensor location or optimized to elicit a desired signal response providing greater resolution for discriminating between the RF characteristics stored in memory as "ground truth" testing data. Generally, the RF sensors will operate in the RF domain, which is defined herein to range from 3 hertz (Hz) to 30 terahertz (THz). In certain embodiments, the RF sensor(s) within the sensor subsystem will operate in the microwave band (herein, defined as ranging from 1 gigahertz (GHz) to 30 GHz). A tradeoff is encountered as data resolution and grain parameter estimate accuracy tends to increase at higher frequencies (e.g., frequencies exceeding 1 GHz), while the cost and complexity of such sensor systems tends to increase at such higher frequencies. For these reasons, in at least some applications, a frequency or frequency range between 1 and 100 GHz is advantageously selected at which to operate each sensor. For example, in such embodiments, a first RF sensor may operate at a first fixed frequency or a maximum frequency (if emitting RF energy over a frequency range) of f1, while a second sensor may operate at a second fixed frequency or a minimum frequency (if emitting RF energy over a frequency range) of f2, with f2 having a value at least twice that of f1.

The RF grain mass and constituent measurement system further includes some form of processing architecture, which is generally referred to hereafter as a "controller." During system operation, the controller receives the RF sensor readings from the RF sensor subsystem and compares such readings to the information (testing data) stored in an RF characteristic database, which resides in a computer-readable memory onboard the combine harvester or otherwise accessible to the controller. As indicated above, the RF characteristic database contains RF characteristic testing data observed for tested grain samples over one or more tested frequency ranges. Such RF characteristic testing data is advantageously generated as a ground truth data by gathering RF signatures or signal response characteristics of a range of grain samples having known properties (e.g., known grain types, known masses or volume measurements, known moisture contents, and known constituent content measurements) over selected frequency ranges encompassing the frequencies at which the RF sensors operate. Such RF characteristic testing data can be stored in a memory accessible to the controller utilizing any suitable data structure, such as multidimensional lookup tables. This notwithstanding, the RF characteristic testing data is conveniently stored in memory as one or more RF signal response maps, which graphically plot RF signal characteristics of the tested grain samples over the tested frequency range(s). The traces of such maps may be stored as discrete plot points or, instead, stored in the form of a multi-variable equations or formulae when possible.

For increased versatility, such RF signal response maps may be generated for grains of various types, grain categories various moisture contents, or the like; and the appropriate RF signal response maps may be recalled by the controller when needed. For example, if determining that the currently-harvested grain is corn having a particular moisture content level (e.g., 16%, by weight), the controller may recall the RF signal response map (or RF characteristic dataset) for the tested corn samples having the specified moisture content; and then utilized the recalled RF signal response map to determine grain mass and a non-moisture constituent content, such as an oil content as set-forth in the example discussed below in connection with FIGS. 4 and 5.

As just indicated, when receiving the RF sensor readings from the RF sensors, the controller then determines grain mass, the moisture content, and/or a non-moisture constituent content of the currently-harvested grain based, at least in part, on a comparison between the RF sensor readings and RF characteristic testing data. In embodiments in which multiple RF sensor readings are captured at different frequencies or frequency ranges, this permits the controller to solve for multiple unknown parameters using simultaneous equations. Without limitation, ratios neural networks, or other techniques may also be used. Thus, utilizing such an approach, the controller may solve for grain volume (for subsequent conversion to grain mass), moisture content, and a first constituent content (e.g., protein, cellulose, starch, or oil content) measurement in embodiments. Additional constituent content levels can also be measured, as desired, by gathering additional RF sensor readings and utilizing an appropriate number of frequency correlation equations or other techniques.

Multiple different RF properties can be observed and utilized in assessing grain characteristics or attributes. By way of non-limiting example, the following principally focuses on RF measurements observed as attenuation (decreases in the amplitude or magnitude of RF energy) and phase change (propagation delay of RF energy). While the following description principally focuses on RF signal response measured in terms of RF energy attenuation and phase change, alternative embodiments of the RF grain mass and constituent measurement system may further consider other RF-related measurements including, but not limited to, polarization, power density distribution, reflection, and back-scattering. After determining the grain mass parameter and the grain constituent quantity estimate, the controller then commands one or more actions based upon the determined grain mass parameter and the grain constituent quantity estimate. Such actions may include any combination of: (i) display of the determined parameters (e.g., as a numerical readout or symbol) on a display device located within an operator cabin of the combine harvester, (ii) storing the determined parameters, as time-stamped data, within a memory accessible to the controller, (iii) offboarding the determined parameters to central control source or other remotely-located entity, and/or (iv) commanding an actuator onboard the combine harvester to adjust a component in a manner responsive to the newly-determined parameters.

By virtue of the above-described functions, embodiments of the RF grain mass and constituent measurement systems achieve multiple notable benefits over conventional sensor systems utilized to measure grain properties within combine harvesters. Real-time grain assessment is enabled by capturing RF signal response readings of the clean grain flow in-situ and without interruption in embodiments in which a first RF sensor captures a first RF signal response of the clean grain stream at an upstream location, while a second downstream RF sensor captures a second RF signal response of the clean grain stream at a downstream location, enabling measurements of essentially the same body of grain. Calibration demands are lessened or eliminated, while the accuracy of grain mass and grain moisture estimates may be maintained, if not enhanced as a result. Usage of sensors operating in the RF domain, and perhaps in the microwave or the MMW domain, avoids grain exposure to higher energy, ionizing EM radiation. Further, and as particularly useful benefit, information can now be gathered in real-time regarding the compositional make-up of grains processed by a combine harvester. For example, the percentage make-up of one or more constituents (e.g., protein, cellulose, starch, oil, or the like) contained within the grain can be determined, opening new possibilities for using such data in various manners.

In some examples, characteristic database may comprise characteristics of non-grain materials that are considered contaminants. The characteristics may comprise absorption, reflectance, backscatter, and other RF properties as a function of frequency. The non-grain materials may comprise metals, plastics, wood, weeds, weed seeds, non-grain plant parts, soil, ash, fungi, biotoxins, genetically modified organisms, or other contaminants.

The following will now describe examples of the RF grain mass and constituent measurement system in the context of an example combine harvester, as illustrated and discussed below in connection with FIGS. 1 and 2. Additionally, methods or processes that may be carried-out by the controller of the RF grain mass and constituent measurement system to determine multiple unknown parameters (grain mass, moisture content, and/or the grain composition of one or more non-moisture constituents) are further discussed below in conjunction with FIG. 3. Finally, examples of RF characteristic testing data that may be stored in the RF characteristic database as RF response maps are further set-forth below in connection with FIGS. 4 and 5. The following description is provided by way of non-limiting illustration only.

Referring to FIG. 1, an example combine harvester 10 (also referred to as agricultural machine 10) equipped with an RF grain mass and constituent measurement system 12 is schematically depicted. The combine harvester 10 is presented by way of illustration to establish a non-limiting example context in which embodiments of the RF grain mass and constituent measurement system 12 may be better understood. In further embodiments, the combine harvester 10 may assume other forms and include different combinations of components suitable for processing crop plants ingested into the harvester 10 when traveling over a field 14. Further, only selected components of the RF grain mass and constituent measurement system 12, such as a controller 16, are shown in FIG. 1 for illustrative clarity. Further illustration and discussion of the example RF grain mass and constituent measurement system 12 is provided below in connection with FIG. 2.

The example combine harvester 10 includes a chassis body or main frame 18, which is supported by a number of ground-engaging wheels 20. The ground-engaging wheels 20 are powered by a non-illustrated engine and drivetrain including, for example, an electronically-controlled hydraulic transmission. Atop a forward portion of the main frame 18, a cabin 22 encloses an operator station including an operator's seat (not shown), at least one display device 24, and an operator interface 26. A feederhouse 28 is mounted to a forward portion of the main frame 18 of the combine harvester 10 at an elevation generally below the cabin 22. Various harvesting heads or, more simply, "headers" are attachable to the feederhouse 28 in an interchangeable manner to, for example, allow customization of the combine harvester 10 for harvesting a particular type of crop. An example of one such header, a harvesting platform 30 is shown in FIG. 1.

As the combine harvester 10 travels over the field 14 in a forward direction, the harvesting platform 30 gathers severed crop plants into the feederhouse 28, which then consolidates the severed crop plants for conveyance (e.g., via a non-illustrated conveyor belt contained in the feederhouse 28) into the interior of the combine harvester 10. Within the combine harvester 10, the crop plants are engaged by a rotating drum conveyor or "beater" 32, which directs the crop plants in a generally upward direction into a rotary threshing and separating section 34. The rotary threshing and separating section 34 can include various components for performing the desired functions of separating the grain and chaff from other plant material. The illustrated rotary threshing and separating section 34, for example, includes a rotor or drum 36 having threshing features and rotatably mounted in a case or rotor housing 38. Rotation of the threshing drum 36 within the rotor housing 38 causes both grain and chaff to fall through the separation grates of a concave 40 and into the inlet of a lower grain cleaning section 42. Concurrently, straw and similar MOG is directed toward an outlet end 44 of the rotary threshing and separating section 34 and is ultimately delivered to another rotating drum or "discharge beater" 46 for expulsion from an aft end of the combine harvester 10.

Discussing now the grain cleaning section 42 in greater detail, this section of the combine harvester 10 includes various components adapted to clean the newly-harvested grain, while separating the chaff therefrom. Such components may include a chaffer 48, a sieve 50, and any number of fans (not shown). By action of the grain cleaning section 42, the newly-cleaned grain is directed into a clean grain elevator 52 for conveyance upwardly into a storage reservoir or clean grain tank 53 of the combine harvester 10. The path traveled by the clean grain from the grain cleaning section 42 to the clean grain tank 53 is referred to herein as a "clean grain flow path," while the grain traveling along this flow path is generally referred to as a "clean grain stream." A number of RF sensors 54, 56, which are included in the RF grain mass and constituent measurement system 12, may be positioned at different locations along the clean grain flow path. For example, the RF sensors 54, 56 may be strategically positioned to capture RF sensor readings of the grain when conveyed through the clean grain elevator 52, as generically indicated in FIG. 1 by the placement of the circular symbols representative of the RF sensors 54, 56. The RF sensors 54, 56 gather RF sensor readings of the newly-harvested grain as the grain is transported into the clean grain tank 53. Such RF sensor readings are then utilized by controller 16 is estimating or calculating grain mass and one or more constituent content levels of the grain, as further discussed below in connection with FIG. 3.

As the clean grain elevator 52 transports the newly-harvested grain into the clean grain tank 53, tailings fall onto a return elevator 58 extending across a lower portion of the clean grain elevator 52. The return elevator 58 then recycles the tailings back to the inlet of the threshing drum 36 for further threshing to allow the above-described grain processing steps to repeat and maximize the grain yield of the combine harvester 10. In this manner, the combine harvester 10 effectively intakes severed crop plants from the field 14, extracts grain from the crop plants, cleans the newly-extracted grain, and then stores the grain in clean grain tank 53 for subsequent unloading utilizing, for example, an unloading auger 60. Also, during usage of the combine harvester 10, certain components within the combine harvester 10 may be positionally adjusted or the operating parameters of such components may be modified utilizing any number of actuators 62, such as hydraulic- or electrically-controlled linear or rotary actuators, one of which is generically represented by symbol 62 in FIG. 1. Such actuators 62 may be controlled in response to operator input received via the operator interface 26 located within the cabin 22, controlled via command signals issued by the controller 16 included in the RF grain mass and constituent measurement system 12, or otherwise commanded by another controller or control unit onboard the combine harvester 10.

Figure 2:
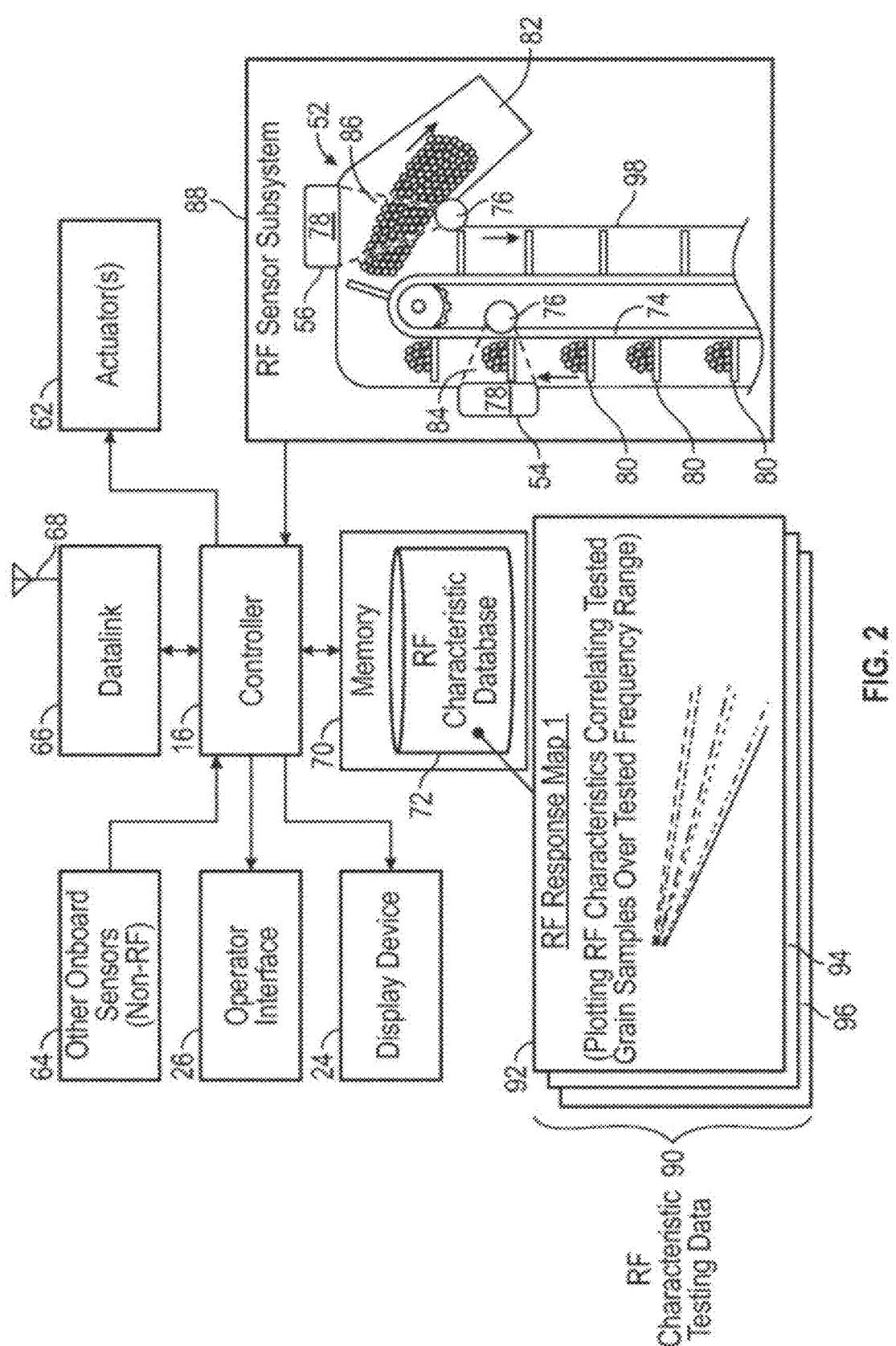
FIG. 2 schematically illustrates additional components that may be included in embodiments of the example RF grain and mass constituent measurement system.

Referring now to FIG. 2, the RF grain mass and constituent measurement system 12 is shown in greater detail, as is an upper section of the clean grain elevator 52. Reference numerals are carried-over from FIG. 1, where appropriate. Note, for example, the inclusion of boxes representative of the controller 16, the display device 24, the operator interface 26, and the RF sensors 54, 56, in the schematic of FIG. 2. In addition to the foregoing components, the RF grain mass and constituent measurement system 12 may further include any number of additional non-RF sensors 64 integrated into the combine harvester 10, a wireless datalink 66 having an antenna 68, and a computer-readable memory 70 storing an RF characteristics database 72. The various data connections between these components are represented in FIG. 2 by a number of signal lines terminating in arrowheads, with such signal lines generally representative of any combination of wired or wireless data connections.

The controller 16 of the RF grain mass and constituent measurement system 12 can assume any form suitable for performing the functions described throughout this document. The term "controller," as appearing herein, is utilized in a non-limiting sense to generally refer to the processing architecture of RF grain mass and constituent measurement system 12. The controller 16 can encompass or may be associated with any practical number of processors, control computers, computer-readable memories, power supplies, storage devices, interface cards, and other standardized components. The controller 16 may also include or cooperate with any number of firmware and software programs or computer-readable instructions designed to carry-out the various process tasks, calculations, and control/display functions described herein. Such computer-readable instructions may be stored within a non-volatile sector of the memory 70 along with the below-described RF characteristic database 72. While generically illustrated in FIG. 2 as a single block, the memory 70 can encompass any number and type of storage media suitable for storing computer-readable code or instructions, as well as other data utilized to support the operation of the RF grain mass and constituent measurement system 12. The memory 70 may be integrated into the controller 16 in embodiments as, for example, a system-in-package, a system-on-a-chip, or another type of microelectronic package or module.

The operator interface 26 located within the cabin 22 can be any device or group of devices utilized by an operator to input commands into or otherwise control the RF grain mass and constituent measurement system 12. In various implementations, the operator interface 26 may be integrated into or otherwise associated with the display device 24. In this regard, the operator interface 26 may include physical inputs (e.g. buttons, switches, dials, or the like) located on or proximate the display device 24, a touchscreen module integrated into the display device 24, or a cursor input device (e.g., a joystick, trackball, or mouse) for positioning a cursor utilized to interface with GUI elements generated on the display device 24. Comparatively, the display device 24 can be any image-generating device configured for operation within the cabin 22 of the combine harvester 10. The display device 24 may be affixed to the static structure of the cabin 22 and realized in a head-down display (HDD) configuration in embodiments. Additionally, in some embodiments, where agricultural machine 10 operates autonomously or semi-autonomously without an operator on board. Operator interface 26 may be provided on a remote device such as a cell phone or tablet computer, connected to agricultural machine 10.

When included in the RF grain mass and constituent measurement system 12, the wireless datalink 66 may assume the form of an RF transceiver permitting wireless data transmission and reception with a remotely-located control center or data source. In various implementations, the datalink 66 can receive information utilized in evaluating crop or soil conditions, weather conditions, and perhaps in periodically updating or refining RF characteristic database 72. Additionally or alternatively, the datalink 66 may be utilized to offboard (that is, transmit to a remotely-located source) data gathered by the controller 16, with the remote source then aggregating the data or other utilizing the data in some manner. In other embodiments, the datalink 66 may be omitted from the RF grain mass and constituent measurement system 12, as may many of the other components shown in FIG. 2.

Lastly, the non-RF sensors 64 may include various sensors providing input data utilized by the controller 16 in assessing one or more parameters pertaining to the currently-harvested grain processed by the combine harvester 10. Such sensors 64 can include, for example, sensors for measuring the speed of the clean grain elevator 52 (as useful in determining mass flow rate) and/or sensors for detecting grain type (useful in filtering the RF characteristic testing data 90 to isolate pertinent RF characteristics in performing the below-described functions to determine grain mass and constituent levels). Additionally, the possibility that the non-RF sensors 64 may include capacitance sensors, weight sensors, or other such sensors utilized to estimate grain moisture content is not precluded. When such sensors are present, the data input provided by the sensors may be utilized to determine moisture content independently of or in combination with RF signal response signals collected by the RF sensors 54, 56, as further described below. In other instances, moisture content may be determined solely utilizing the RF signal response signals provided by the RF sensors 54, 56; or determined in another manner, such as by operator input received via operator interface 26.

Discussing RF sensors 54, 56 in greater detail, the RF sensors 54, 56 each include at least one RF emitter 76 and at least one RF receiver 78. As indicated above, the RF sensors 54, 56 are usefully disposed at different locations along the clean grain flow path; although one or both of the RF sensors 54, 56 can be potentially positioned to capture RF sensor readings of the harvested grain outside of the clean grain flow path in alternative embodiments. In various implementations, and as indicated on the right of FIG. 2, the RF sensors 54, 56 are integrated into the structure of the clean grain elevator 52. Specifically, the RF sensor 54 may be strategically positioned to capture RF sensor readings of the harvested grain when transported upwardly within the clean grain elevator as piles or consolidated masses supported by the grain elevator paddles 80 (only a few of which are labeled in FIG. 2) projected from a conveyor belt 74 contained in the clean grain elevator 52. Comparatively, the RF sensor 56 may be positioned to capture the harvested grain as the grain is thrown from the paddles 80 and thus discharged through an outlet 82 of the clean grain elevator 52. Accordingly, in such embodiments, the interrogation area or FOV 84 of the RF sensor 56 may be enlarged relative to the interrogation area or FOV 86 of RF sensor 54 to ensure that the RF sensor 56 records the signal response of substantially all of the airborne grain passed through the outlet section 82 of the clean grain elevator 52. This may be accomplished by tailoring the respective antennae shapes and dimensions of the emitter 76 and receiver 78. In still other embodiments, the RF sensors 54, 56 may be positioned at the same location or essentially the same location within the clean grain elevator 52; e.g., the sensors 54, 56 may be co-located to capture RF sensor readings of the grain when supported by a paddle 80 of the clean grain elevator 52 or co-located to capture RF sensor readings of the grain when discharged from the clean grain elevator 52 through outlet 82. Collectively, the RF sensors 54, 56 included in the RF grain mass and constituent measurement system 12 form an RF sensor subsystem 88.

In embodiments, the RF sensors 54, 56 concurrently capture RF sensor readings of the currently-harvested grain, while transported along the clean grain flow path. Further, the RF sensor 54 is configured to capture RF sensor readings of the currently-harvested grain at a first frequency or frequency range. Comparatively, RF sensor configured to capture RF sensor readings of the currently-harvested grain at a second frequency or frequency range different than the first frequency or frequency range. The sensors 54, 56 can operate in either or both of a transmit and a reflected mode. Additionally or alternatively, the RF sensors 54, 56 may each be configured to capture RF sensor readings of the grain when subjected to or impinged with RF energy falling within the Terahertz band. For example, in such embodiments, a first RF sensor may operate at a first fixed frequency or a maximum frequency (if emitting RF energy over a frequency range) of f1, while a second sensor may operate at a second fixed frequency or a minimum frequency (if emitting RF energy over a frequency range) of f2. Further the value of f2 may be at least twice that of f1. The frequencies at which the RF sensors 54, 56 operate will vary among embodiments, as will the sensor positioning; generally, however, the sensor frequencies and positioning are selected to maximize signal-to-noise ratios, avoid structural (e.g., metallic) interface, and elicit distinct signal responses from the grain to optimize resolution when distinguishing between the RF characteristics stored in RF characteristic database 72, as further discussed below in connection with FIGS. 3-5.

The RF sensor readings captured by the RF sensors 54, 56 are provided over wired or wireless data connections to the controller 16. The controller 16 then considers the RF sensor readings provided by the RF sensors 54, 56 in conjunction with data contained within the RF characteristic database 72 in assessing unknown parameters pertaining to the grain processed by the combine harvester 10. Specifically, the RF characteristic database 72 contains RF characteristic testing data 90 observed for tested grain samples having known properties, while the grain samples are impinged with RF energy over one or more tested frequency ranges. An "RF signal response" can be any RF signal measurement captured when impinging RF energy against a harvested grain, whether the RF energy is passed through or reflected from the grain. The RF signal response may be, for example, a measurement of: (i) the attenuation of RF energy when passed through the harvested grain; or (ii) the propagation delay (phase shift) of RF energy when passed through the harvested grain. In further implementations, other types of RF signal responses may be considered in addition to or in lieu of the attenuation and/or propagation delay of RF energy impinged against the harvested grain. A non-exhaustive list of such alternative RF signal responses that may be considered by the controller 16 includes polarization, power density distribution, reflection, and back scattering. The controller 16 utilizes such RF sensor readings to determine mass and one or more constituent quantities (e.g., moisture content and/or one or more non-moisture content percentages) of the harvested grain based, at least in part, on a comparative analysis with the RF characteristic testing data 90 stored in the database 72.

The RF characteristic testing data 90 may be stored as one or more RF signal response maps 92, 94, 96, as generally indicated in the lower left of FIG. 2. Alternatively, the RF characteristics may be stored utilizing another data structure, such as a multidimensional lookup table. When stored in one or more response maps 92, 94, 96, the RF characteristics may be plotted as traces, lines, or curves on a two-dimensional graph of frequency range versus measured RF signal response parameter. Such traces can be stored as series of discrete, connected points or coordinates; or stored in the form of formulae when possible. Examples of such RF signal response maps are discussed more fully below in connection with FIGS. 4 and 5. The RF characteristic database 72 may store a plurality of such maps associated with or corresponding to different grain types, with controller 16 then selecting the appropriate response map or maps (e.g., the response map 92 shown in the foreground in FIG. 2) based upon the type or category of grain currently processed by the combine harvester 10. Subsequently, the controller 16 may determine or estimate the grain mass, the moisture content, and/or a first constituent content of the currently-harvested grain based, at least in part, on matching the RF sensor readings with a specific RF signal response included in the RF signal responses plotted on the RF signal response map 92. The manner in which the controller 16 may perform such function will now be described in more detail in connection with FIG. 3.

Figure 3:
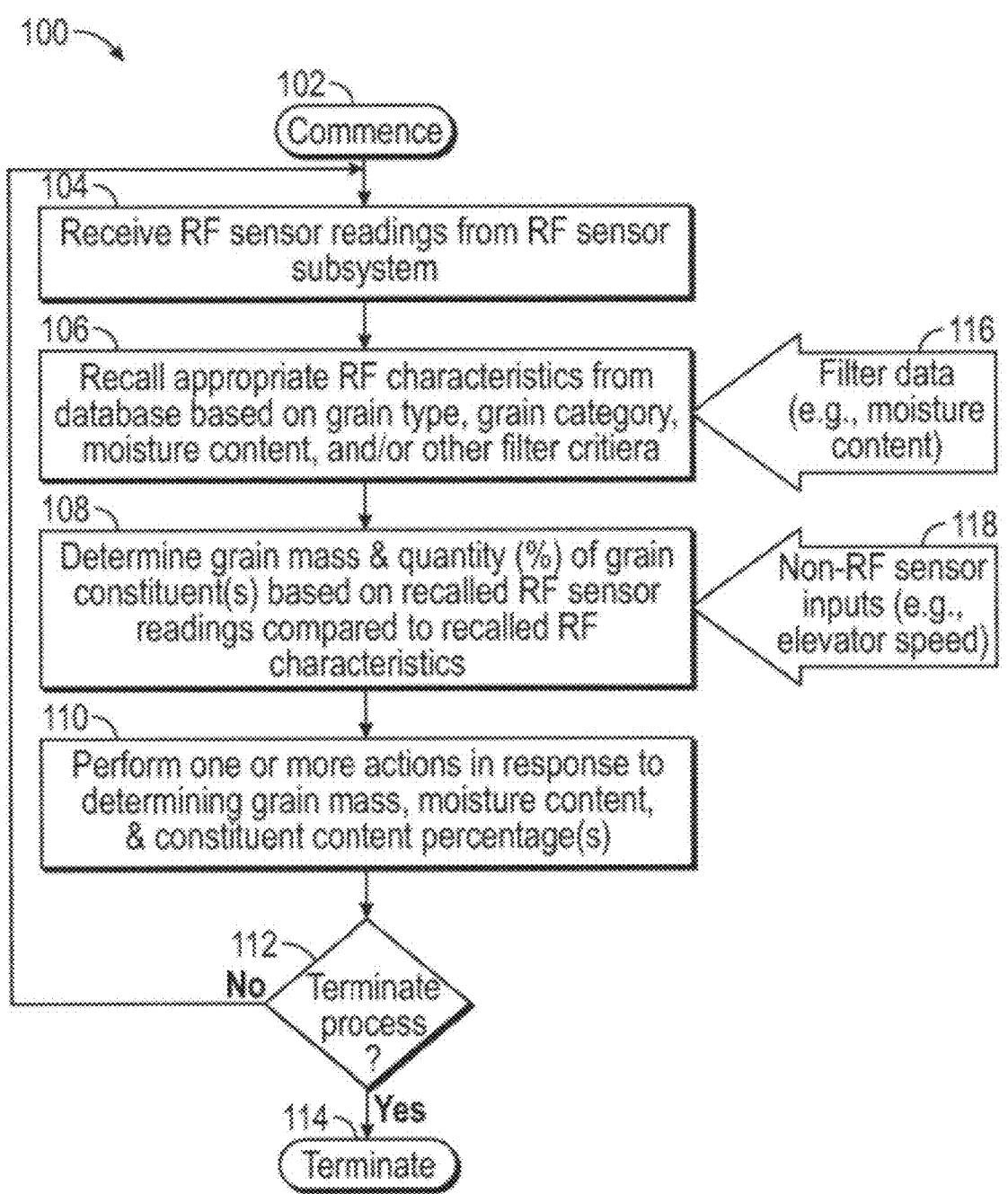
FIG. 3 is a flowchart of an example process suitably carried-out by a controller of the RF grain and mass constituent measurement system (FIGS. 1 and 2) to determine multiple parameters (e.g., grain mass, moisture content, and/or constituent content levels) of a grain processed by the combine harvester shown in FIG. 1.

Referring now to FIG. 3, an RF grain mass and constituent measurement process 100 is presented in accordance with a non-limiting example embodiment. The RF grain mass and constituent measurement process 100 can be carried-out by the controller 16 of the RF grain mass and constituent measurement system 12 in embodiments of the present disclosure. The RF grain mass and constituent measurement process 100 includes a number of process STEPS 102, 104, 106, 108, 110, 112, 114, each of which is described, in turn, below. Depending upon the particular manner in which the RF grain mass and constituent measurement process 100 is implemented, each step generically illustrated in FIG. 4 may entail a single process or multiple sub-processes. Further, the steps illustrated in FIG. 3 and described below are provided by way of non-limiting example only. In alternative embodiments of the RF grain mass and constituent measurement process 100, additional process steps may be performed, certain steps may be omitted, and/or the illustrated process steps may be performed in alternative sequences.

The RF grain mass and constituent measurement process 100 commences at STEP 102 in response to the occurrence of a predetermined trigger event. In certain instances, the trigger event may be detection of the intake of severed crop plants into the combine harvester 10 (FIG. 1). In other instances, the RF grain mass and constituent measurement process 100 may be commence in response to a different trigger event, such as in response to operator input received via operator interface 26 indicating that the RF grain mass and constituent measurement process 100 is desirably performed.

After commencing (STEP 102), the RF grain mass and constituent measurement process 100 advances to STEP 104. At STEP 104, the controller 16 receives RF sensor readings from RF sensor subsystem 88 (FIG. 2). In the illustrated example, specifically, the controller 16 receives RF sensor readings from RF sensors 54, 56 positioned in the clean grain elevator 52 during STEP 104. Next (or concurrent with or prior to STEP 104), the controller 16 recalls appropriate RF characteristics from the RF characteristic database 72 (FIG. 2). As indicated in FIG. 3 by arrow 116, controller 16 may determine the pertinent RF characteristics for recollection and subsequent consideration utilizing various types of filter criteria. Generally, in embodiments, the RF characteristic database 72 may contain multiple datasets of RF characteristics, with each dataset corresponding to a particular type of grain or a particular grain category. In such embodiments, the controller 16 may identify the particular grain type or grain category presently processed by the combine harvester 10; e.g., based upon operator input received via operator interface 26, based on GPS data if correlated to grain type, and/or based on any type of automated grain identification technique, such as image processing of a live camera feed or surface response measurements of the harvested grain. Examples of grain types include, but are not limited to, corn, canola, soybeans, wheat, oats, and sunflowers. Grain categories may be differentiated by general grain compositions, such as protein- or oil-rich grains. The controller 16 may then extract the appropriate RF characteristics from the database 72 tagged or linked to the presently-processed grain type or category. A similar approach can also be utilized to filter by moisture content after a moisture content has been estimated by the controller 16, as described below. In other embodiments, other filter criteria can be utilized; or the controller 16 may simply compare all RF characteristics stored in the database 72 to the RF sensor readings during subsequently-performed STEP 108.

Next, at STEP 108 of process 100 (FIG. 3), the controller 16 determines multiple unknown parameters describing the currently-processed grain harvested by the combine harvester 10. In various embodiments, such parameters will include grain mass and the fraction of the harvested grain composed of a particular constituent type or types; e.g., protein, cellulose, starch, or oil content. The controller 16 also usefully estimates moisture content of the harvested grain during or prior to STEP 108 and then compensates for the moisture content estimate in determining grain mass and constituent content level(s) for increased accuracy. In embodiments, the controller 16 may utilize the RF sensor readings provided by RF sensors 54, 56 to estimate moisture content; e.g., by comparing the RF sensor readings 54, 56 to the recalled RF characteristics for tested grain samples having known moisture contents of varying levels. Further discussion in this regard is provided below in connection with FIG. 4. In other instances, moisture content may be determined in another manner; or any such moisture content estimate rendered utilizing the RF sensor data may be blended with other moisture content estimates, if available. Generally, then, various types of non-RF sensor data input 118 may be considered by the controller 16 during STEP 108, as indicated by arrow 118. In instances in which such data input 118 includes operator input indicative of moisture content, weight or capacitance measurements indicative of moisture content, or other such information indicative of moisture content, this data may alternatively be utilized to determine moisture content or otherwise considered during STEP 108.

The RF sensor readings are compared to the recalled RF characteristics to estimate grain mass and one or more constituent quantities within the harvested grain. The controller 16 may identify a particular characteristic based upon the RF sensor readings to determine unknown parameters (grain mass and grain attribute(s)), noting that the usage of multiple RF sensor readings captured at different frequencies or frequency ranges enables multiple unknown parameters to be discerned utilizing cross-reference techniques. Stated differently, the controller 16 may analyze the RF sensor readings utilizing the recalled RF characteristic or correlation equations (as established by the testing data); e.g., top-bottom and in-out measurements can be utilized to device multiple variables for the constituents in embodiments. With respect to grain mass, in particular, the RF sensor readings may be utilized to initially determine a volume of grain as the grain passes through a given sensor interrogation area. This may be expressed as, for example, a grain pile depth in the case of RF sensor 54 shown in FIG. 2, which can then be converted to a volumetric measurement as the width and length of the grain pile is generally known (determined by the configured space between the grain elevator housing 98, the paddles 80, and the conveyor belt 74). The grain volume of each grain pile can then be converted to mass (e.g., number of grams) utilizing a known conversion factor, which may then be converted to grain mass flow rate and crop yield by considering the speed of the clean grain elevator 52 (further included in the non-RF sensor data inputs 118) and other such factors.

After determining grain mass, moisture content, and the constituent content(s) of the currently-harvested grain (STEP 108), the controller 16 progresses to STEP 110 and performs any number of actions. Such actions may include any combination of the following: (i) displaying such information on the display device 24 for reference by an operator; (ii) storing such information in memory 70 to create, for example, a time-stamped data log for subsequent reference or analysis; (iii) offboarding such information to another entity or system via the datalink 66; or (iv) commanding actuator(s) 62 to adjust an operating parameter or component position in response to changes in the grain mass flow rate and/or moisture content. Following STEP 110, the controller 16 determines whether the RF grain mass and constituent measurement process 100 should terminate (STEP 112) due to, for example, deactivation by an operator or cessation of crop harvesting by the combine harvester 10. If it is determined that the RF grain mass and constituent measurement process 100 should terminate, the controller 16 terminates the process 100 accordingly. Otherwise, the controller 16 returns to STEP 104 and performs a further iteration of the RF grain mass and constituent measurement process 100, as previously described. Such steps may be performed on a relatively rapid basis to allow the RF grain mass and constituent measurement system 12 to measure grain mass and constituent levels (moisture content and/or non-moisture content level(s)) in highly responsive, real-time manner.

Figure 4:
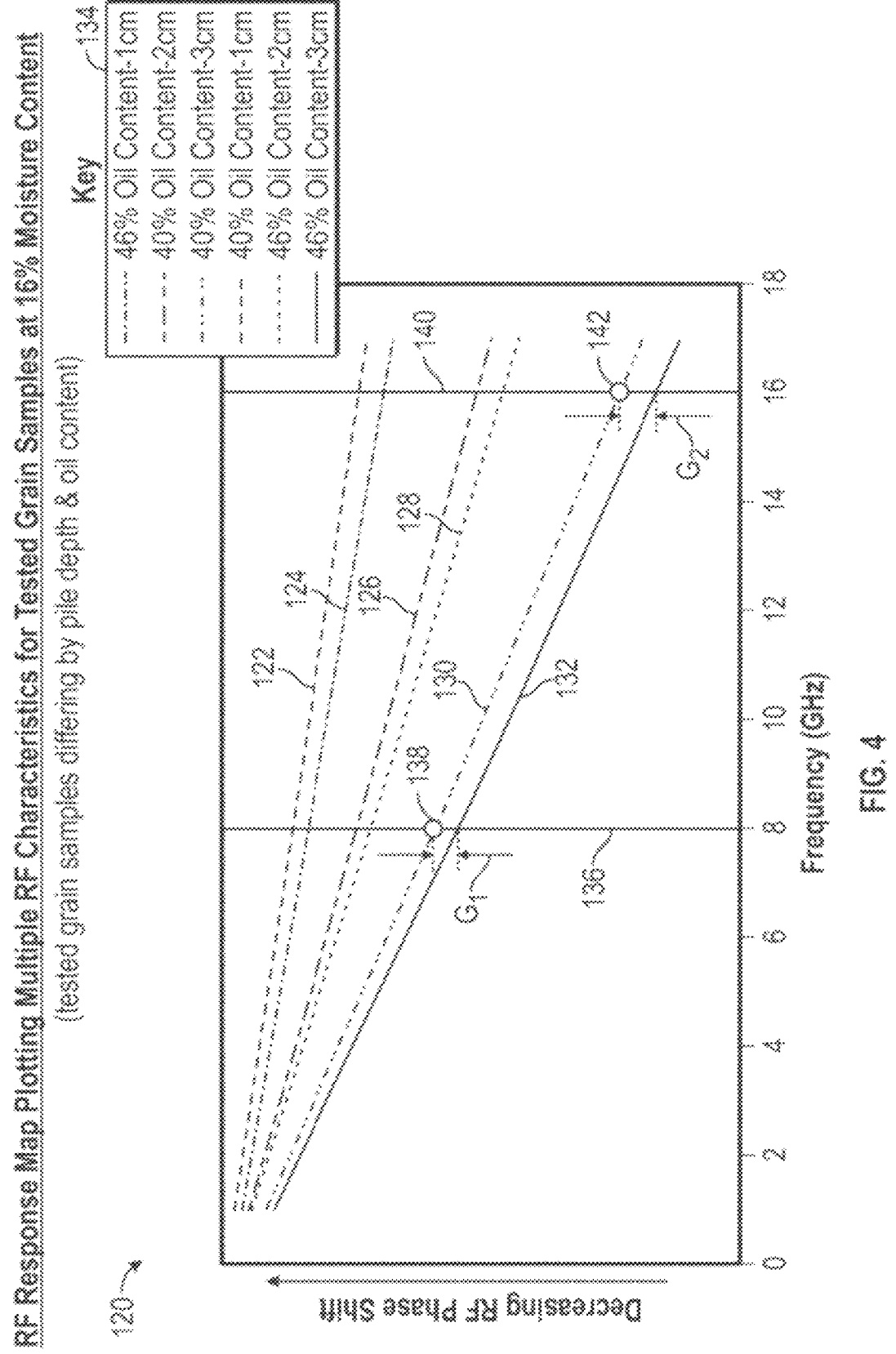
FIG. 4 graphically plots RF characteristics (here, expressed in terms of phase shift) over a tested frequency range for a number of tested grain samples, which may be utilized by the controller in determining grain mass and a first constituent content (here, oil content) in embodiments.

FIG. 4 presents an example RF response map 120 plotting several RF signal response characteristics 122, 124, 126, 128, 130, 132 over a tested frequency range for a number of tested grain samples. Specifically, in the illustrated example, each of the tested grain samples corresponding to the RF characteristics 122, 124, 126, 128, 130, 132 have a known moisture content of 16%, by weight. In addition to a known moisture content, the tested grain samples also include known oil content levels and pile depths in the illustrated example, as indicated by a key 134. In the case of RF response map 120, the RF signal response under consideration is the propagation delay or phase shift of RF energy when impinged against (e.g., passed through) the tested grain samples. Various other RF response characteristics for tested grain samples having 16% moisture content, varying oil levels, and/or varying pile depths may also be plotted on the example RF response map 120 in embodiments, but are not shown in FIG. 4 for visual clarity.

Referring to FIGS. 1-3 in combination with FIG. 4, the controller 16 may estimate moisture content of the currently-harvested grain during STEP 106 of the RF grain mass and constituent measurement process 100 (FIG. 3) in embodiments. Again, the controller 16 may determine moisture content in any suitable manner, but usefully does so utilizing multiple correlations established by the stored testing data and multiple sensor readings captured by the RF sensors 54, 56. For example, the RF signal response characteristics 122, 124, 126, 128, 130, 132 plotted by the RF response map 120 for tested grain sample having an established moisture content level may be considered in conjunction with multiple other plotted RF signal response characteristics 122 (or correlation equations) having other established moisture content levels. The current RF sensor readings, as captured for different frequencies or frequency ranges, may then be utilized to identify the moisture content level by geometric or pattern matching to a particular characteristic or range of candidate characteristic. The determined moisture level may then be utilized to select the RF response map 120 for usage in evaluating the pile depth and the oil content level of the currently-processed grain. For example, in an embodiment in which an RF sensor reading is captured at a frequency of 8 GHz (as indicated in FIG. 4 by a vertical line 136), a detected phase shift (unit-less in FIG. 4, but suitably expressed in degrees) may correspond to a marker 138. As the marker 138 falls on or adjacent the characteristic 130, it can be determined that currently-harvested gran has a pile depth of 2 centimeters (cm) and an oil content level of approximately 46% by weight. Once determined, the pile depth can be converted into volume for usage in determining grain mass. A similar approach can also be utilized to determine the other constituent content levels of the currently-harvested grain, as permitted by the RF sensing readings and the RF characteristic testing data stored in the database 72.

In the above-described example, a fixed testing frequency of 8 GHz was discussed. Referring further to FIG. 4, vertical line 140 further denotes a testing frequency of 16 GHz, with marker 142 indicating a hypothetical phase shift value taken along the characteristic or trace 130 that may be detected in an alternative practice scenario. Thus, in either case, the RF sensor readings indicate that the currently-harvested grain has a pile depth of 2 cm (as divided into a discrete pile supported by one of the paddles 80 of the clean grain elevator 52) and an oil content of approximately 46%, by weight. However, as may be appreciate by comparing the vertical spacing between the characteristic 130 and the next closest characteristic 132 (identified as "G1" for 8 GHz and "G2" for 16 GHz in FIG. 4, "G" denoting "gap"), the separation or resolution between characteristics increases with increasing frequency. Considering this, there is a general benefit to impart the RF sensors 54, 56 with operational frequencies or frequency ranges that are higher to enhance resolution and accuracy. Concurrently, however, the cost and complexity of RF sensors tends to also increase at higher frequencies falling with the RF domain. For these reasons, in at least some applications, the RF sensors 54, 56 each operate at distinct frequencies or frequencies ranges between 1 and 100 GHz in embodiments. In other embodiments, however, one or both of the RF sensors 54, 56 may operate outside of the aforementioned range, providing that sensors 54, 56 operate within the RF domain.

In the example of FIG. 4, an RF sensor reading captured at a single fixed RF frequency or fixed RF frequencies is considered. In further embodiments, RF sensor 54 and/or RF sensor 56 may capture RF sensor readings over a predetermined frequency range and, thus, generate an RF response signature for the currently-harvested grain. The controller 16 may then geometrically match (e.g., utilizing a pattern matching image analysis algorithm) the sensor-detected RF signature to a corresponding RF signature or characteristic contained in the RF characteristic database 72. An example of such an RF response characteristic 146 is plotted in an RF response map 144 shown in FIG. 5. In the map 144, detected changes in RF wave magnitude or amplitude (and thus attenuation) is charted on the vertical axis, while frequency is charted on the horizontal axis. While the magnitude axis is unit-less in the illustrated example (though the magnitude increase may be logarithmic), decibels or a similar unit may be utilized in actual implementations. Further, in other embodiments, a different RF response (e.g., phase shift, back scattering, polarization, reflection, power distribution, or a combination thereof) can be charted in a similar manner Distinct geometric features that may be utilized for comparative analysis include a nadir occurring at a particular minimum magnitude (MMIN) and a corresponding frequency (f1), as identified by marker 148. Additionally, pronounced changes in slope (as indicated by markers 150) on either side of the nadir marker 148 may be considered by location or by spacing in the frequency dimension (as indicated by double-headed arrow 152). Thus, by matching such a sensor reading with a similar, if not identical RF characteristic or signature contained within the RF characteristic database 72, the controller 16 may identify the currently-harvested grain as sharing the same properties (e.g., pile depth, moisture content, and/or consistent content level) as does the tested grain sample corresponding to the identified RF characteristic or signature 146.

Through the above-described comparative analysis of the RF sensor readings with the testing data stored in the RF characteristic database 72, grain mass and grain constituent measurements can be determined by the RF grain mass and constituent measurement system 12 in a highly accurate and responsive manner. Further, such grain parameters can be determined in real-time or near real-time, while minimizing calibration requirements through the usage of ground truth data as consolidated into the reference models or characteristics stored as RF characteristic testing data. The foregoing process steps are presented by way of illustration only and should be considered non-limiting, noting that other processing techniques may be employed in further embodiments enabling grain mass and grain attributes (moisture and/or non-moisture content levels) to be determined by comparative analysis of RF sensor readings to "ground truth" or testing data stored in an RF characteristic database located onboard the combine harvester or otherwise accessible to the controller 16 of the RF grain mass and constituent measurement system 12.

While the embodiments described above generally provides an RF grain mass and grain constituent measurement system to obtain grain mass and grain constituent measurements, additional embodiments using Terahertz electromagnetic radiation can detect additional features of the harvested material and/or crop. For example, configuring one or both of sensors 54, 65 (shown in FIGS. 1 and 2) to utilize Terahertz electromagnetic radiation can provide the ability to detect additional characteristics in the harvested crop, such as the presence of a genetically modified organism (GMO). Further, the placement of an RF sensor in locations of the harvester beyond the clean grain stream can allow additional information about the harvested material to be detected. For example, placing a Terahertz-based sensor at any of locations 200, 202, or 204 (shown in FIG. 1) allows sensing of additional aspects relative to the harvesting operation. With a Terahertz-based sensor located at location 200, early detection of materials can be accomplished such that the harvester can react to avoid damaging the front/feeding components. Positioning the Terahertz-based sensor at location 204 can provide additional material relative to the clean grain stream, such as the presence of GMO's, pesticide residue, fungus, and/or soil/ash. Finally, positioning the Terahertz-based sensor at location 202 can provide useful information when using an implement or attachments behind the harvester. For example, a Terahertz-based sensor at location 202 can detect weed seed. Terahertz-based sensors are particularly effective at sensing non-ferrous foreign material, which is highly useful in harvesting.

Figure 6:
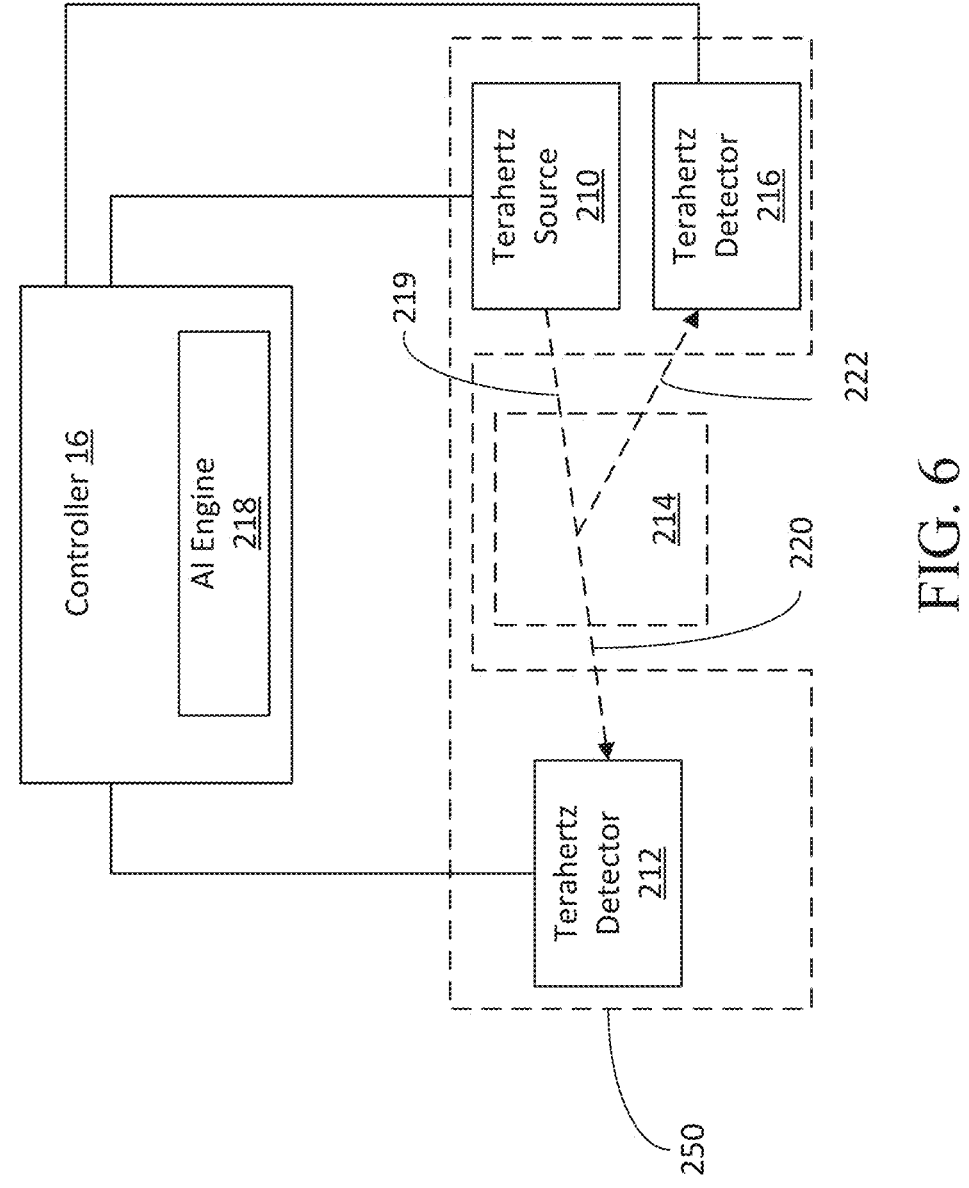
FIG. 6 is a diagrammatic view of a Terahertz-based sensor in accordance with one embodiment.

FIG. 6 is a diagrammatic view of a Terahertz-based sensor in accordance with one embodiment. As shown in FIG. 6, Terahertz-based sensor 250 includes Terahertz source 210 and one or more Terahertz detectors 212, 216. Source 210 is disposed to direct Terahertz electromagnetic radiation 219 through a detection area 214 to one or more detectors 212, 214. In some embodiments, sensor 250 may only detect attenuation of Terahertz electromagnetic radiation 219 after passing through detection area 214, in which case a single detector 212 may be used and positioned to receive the attenuated Terahertz electromagnetic radiation 220. In other embodiments, sensor 250 may only detect reflection of the Terahertz electromagnetic radiation 219 from material within detection area 214, in which case a single detector 216 may be used and positioned to receive the reflected Terahertz electromagnetic radiation 222. Of course, embodiments also include using both such detectors 212, 214 to detect attenuated Terahertz electromagnetic radiation 220 as well as reflected electromagnetic radiation 222. Further, those skilled in the art will appreciate that additional/alternate Terahertz detectors can used to detect other types of interactions, such as backscatter.

Terahertz source 210 can be any suitable device capable of Terahertz electromagnetic radiation to detection area 214. Examples, of such suitable devices include, without limitation, a femtosecond Ti-sapphire laser, a Yttrium Iron Garnet (YIG)-oscillator, a quantum cascade laser, a P-type germanium laser, a silicon-based laser; a free electron laser, a photoconductive switch, optical rectification, a backward-wave oscillator, a transferred electron device (i.e., Gunn diode), and a resonant tunneling diode. In embodiments where a number of frequencies within the Terahertz range (0.1-30 Terahertz) are desired, a variable frequency source can be used, such as a variable frequency quantum cascade laser. In other embodiments, a plurality of sources 210 can be used with each source 210 having a different band within the Terahertz range. Additionally, it is expressly contemplated that source 210 may operate in a pulsed mode or a continuous wave mode.

Detectors 212, 214 can be any suitable device that can detect electromagnetic radiation in the Terahertz range. Detectors 212, 214 may be configured to provide measurement in the frequency domain or the time domain to controller 16. Examples of detectors 212, 214 include, without limitation, a photoconductive semiconductor, free-space electro-optic sampling using ZnTe and BBO crystals, bolometer, an interferometer, Schottkey diode, backward diode, High-Electron-Mobility-Transistor (HEMT), Golay cell, and a pyroelectric detector.

Terahertz sensor 250 provides a signal that contains significant information about the material that the Terahertz electromagnetic radiation has passed through and/or reflected from. As shown in FIG. 6, the detector(s) 212, 214 are operably coupled to controller 16, which may include or be coupled to artificial intelligence engine 218. Utilizing engine 218 allows controller 16 to perform relatively high level classifications based on the received signal(s). Engine 218 may employ any suitable artificial intelligence and/or machine learning techniques in the provision of such classification. Examples of suitable artificial intelligence techniques include, without limitation, memory networks, Bayes systems, decisions trees, Eigenvectors, Eigenvalues and Machine Learning, Evolutionary and Genetic Algorithms, Expert Systems/Rules, Support Vector Machines, Engines/Symbolic Reasoning, Generative Adversarial Networks (GANs), Graph Analytics and ML, Linear Regression, Logistic Regression, LSTMs and Recurrent Neural Networks (RNNSs), Convolutional Neural Networks (CNNs), MCMC, Cluster Analysis, Random Forests, Reinforcement Learning or Reward-based machine learning. Artificial intelligence engine 218 may also utilize mathematical techniques such as formulas, simultaneous linear equations, statistical thresholds, ratios, and other techniques. Learning may be supervised or unsupervised.

While a single sensor 250 is shown in FIG. 6 operably coupled to controller 16, multiple such sensors located at different positions on the harvester may be coupled to controller 16 such that AI engine 218 receives input from a plurality of Terahertz-based sensors. Additionally, any of the sensors described above may be used to provide additional inputs to AI engine 218 for enhanced operation and classification. Further, other types of sensors, such as one or more chemical or chemometric sensors may also be used as additional inputs to AI engine 218.

Figure 7:
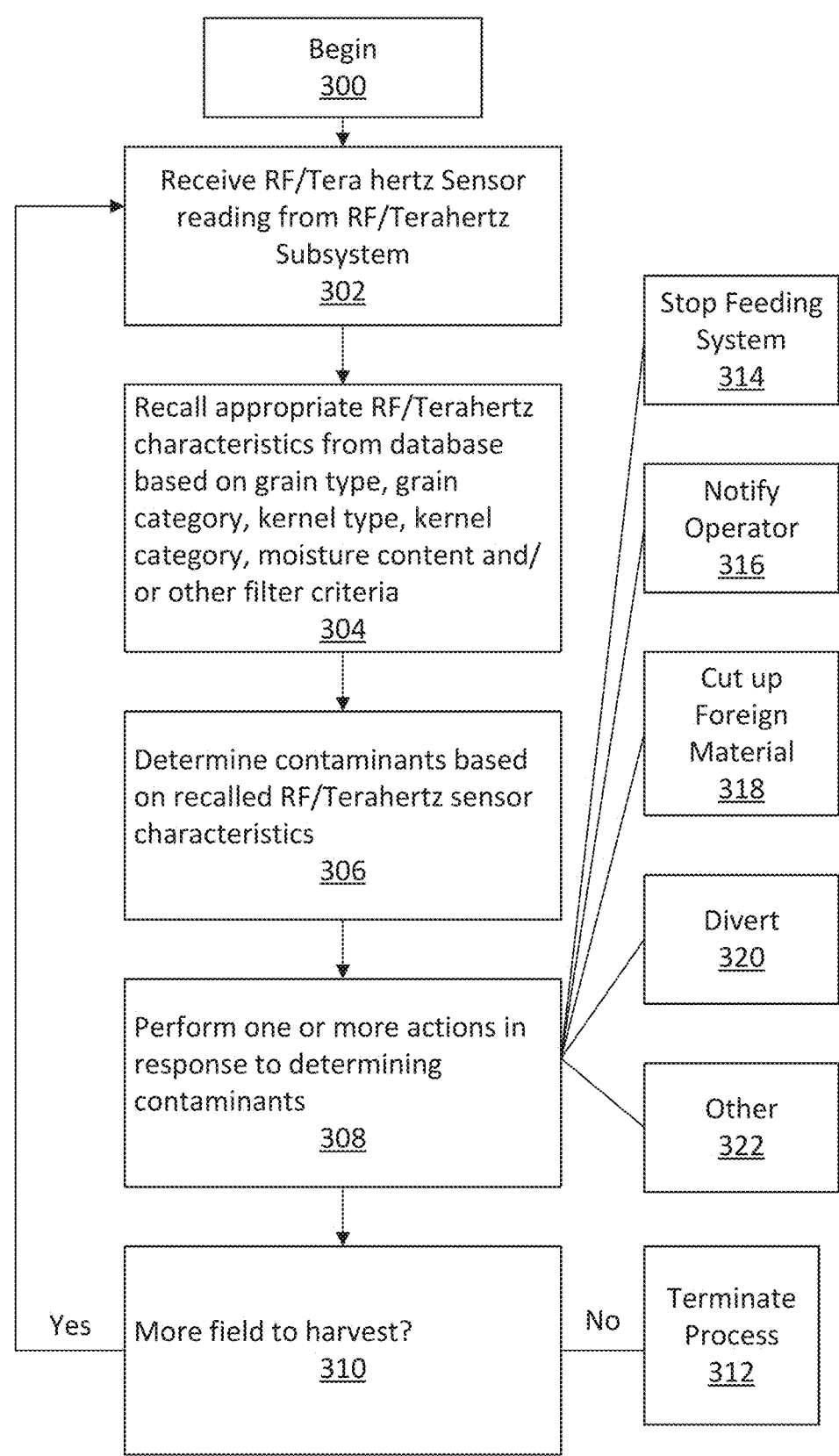
FIG. 7 is a flowchart of an example process suitably carried-out by a controller to determine one or more parameters of a crop harvest operation performed by the combine harvester shown in FIG. 1.

FIG. 7 is a flowchart of an example process carried out by controller 16 to determine one or more parameters of a crop harvest operation related to the harvester shown in FIG. 1. The method begins at block 300 102 in response to the occurrence of a predetermined trigger event. In certain instances, the trigger event may be detection of the intake of severed crop plants into the combine harvester 10 (FIG. 1). In other instances, the method may commence in response to a different trigger event, such as in response to operator input received via operator interface 26.

After commencing (block 300), control transfers to block 302, where controller 16 receives RF sensor readings from one or more Terahertz-based sensors. Additionally, readings may also be received from RF sensor subsystem 88 (FIG. 2). In the illustrated example, specifically, the controller 16 receives sensor readings from Terahertz-based sensor 250. Next, at block 304, controller 16 recalls appropriate characteristics from the characteristic database 72 (FIG. 2). Characteristics can include, without limitation, characteristics of non-grain materials that are considered contaminants. The characteristics may comprise absorption, reflectance, backscatter, and other RF properties as a function of frequency. The non-grain materials may comprise metals, plastics, wood, weeds, weed seeds, non-grain plant parts, soil, ash, fungi, biotoxins, genetically modified organisms, or other contaminant. Controller 16 may determine the pertinent characteristics for recollection and subsequent consideration utilizing various types of filter criteria. Generally, in embodiments, the characteristic database 72 may contain multiple datasets of characteristics, with each dataset corresponding to a particular type of grain or a particular grain category. In such embodiments, the controller 16 may identify the particular grain type or grain category presently processed by the combine harvester 10; e.g., based upon operator input received via operator interface 26, based on GPS data if correlated to grain type, and/or based on any type of automated grain identification technique, such as image processing of a live camera feed or surface response measurements of the harvested grain. Examples of grain types include, but are not limited to, corn, canola, soybeans, wheat, oats, and sunflowers. Grain categories may be differentiated by general grain compositions, such as protein- or oil-rich grains. The controller 16 may also identify a kernel category and/or a kernel type. The controller 16 may then extract the appropriate characteristics from the database 72 tagged or linked to the presently-processed grain type or category. A similar approach can also be utilized to filter by moisture content after a moisture content has been estimated by the controller 16, as described below. In other embodiments, other filter criteria can be utilized; or the controller 16 may simply compare all characteristics stored in the database 72 to the sensor readings during a subsequently-performed step.

Next, at block 306, controller 16 determines one or more parameters relative to the currently harvest operation of the combine harvester 10. In various embodiments, such parameters will include foreign object/material detection, contaminant (e.g., pesticide, fungus, GMO, soil/ash) presence and/or level. Additionally, controller 16 may also determine one or more of grain mass and the fraction of the harvested grain composed of a particular constituent type or types; e.g., protein, cellulose, starch, or oil content. In embodiments, controller 16 may utilize the sensor readings provided by one or more Terahertz-based sensors. Controller 16 may determine the above-noted parameters using a suitable artificial intelligence classifier, such as AI engine 218 (shown in FIG. 6). Additionally, various additional types of sensor data input 118 may be provided to AI engine 218 and considered by the controller 16 during block 306.

At block 308, controller 16 performs one or more actions based on the one or more parameters determined at block 306. Examples of actions include, without limitation, stopping the feeding system of the harvester, as indicated at block 314. This can allow the operator to pause the harvesting operation and remove any non-crop material, such as non-ferrous foreign material, from the feeder. Additionally or alternatively, controller 16 may notify the operator of the one or more parameters, as indicated at block 316. This notification, may include the display of parameter levels on a display device within the cab of the harvester. However, such notification may also include an audible or visual alarm indicating the determination of one or more parameters above a certain threshold. As indicated at block 318, another action that controller 16 may perform is to the continue running the compressor/cutting operation to reduce the detected foreign material size in order to pass through for the livestock and material processing. As indicated at block 320, controller 16 may command a diverter or positioner to direct contaminated materials to a different chamber other than cutting process, so that the contaminated material can be cleaned up manually/automatically. In addition to the actions described with respect to blocks 314, 316, 318, and 320, controller 16 may take other suitable actions as well or instead, as indicated at block 322.

After performing one or more actions in response to determining contaminants (block 308), controller 16 progresses to block 310 and performs any number of actions.

Such actions may include any combination of the following: (i) storing such information in memory 70 to create, for example, a time-stamped data log for subsequent reference or analysis; (ii) offboarding such information to another entity or system via the datalink 66; or (iii) commanding actuator(s) 62 to adjust an operating parameter or component position in response to the one or more parameters and/or detection of contaminants. At block 310, controller 16 also determines whether the process should terminate due to, for example, deactivation by an operator or cessation of crop harvesting by the combine harvester 10. If it is determined that the process should terminate, controller 16 terminates the process accordingly, as indicated at block 312. Otherwise, controller 16 returns to block 302 and performs a further iteration. Such steps may be performed on a relatively rapid basis to allow the system to be highly responsive and allow real-time detection and handling of contaminants.

It will be noted that the above discussion has described a variety of different systems, components and/or logic. It will be appreciated that such systems, components and/or logic can be comprised of hardware items (such as processors and associated memory, or other processing components, some of which are described below) that perform the functions associated with those systems, components and/or logic. In addition, the systems, components and/or logic can be comprised of software that is loaded into a memory and is subsequently executed by a processor or server, or other computing component, as described below. The systems, components and/or logic can also be comprised of different combinations of hardware, software, firmware, etc., some examples of which are described below. These are only some examples of different structures that can be used to form the systems, components and/or logic described above. Other structures can be used as well.

The present discussion has mentioned processors, processing systems, controllers and/or servers. In one example, these can include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 8:
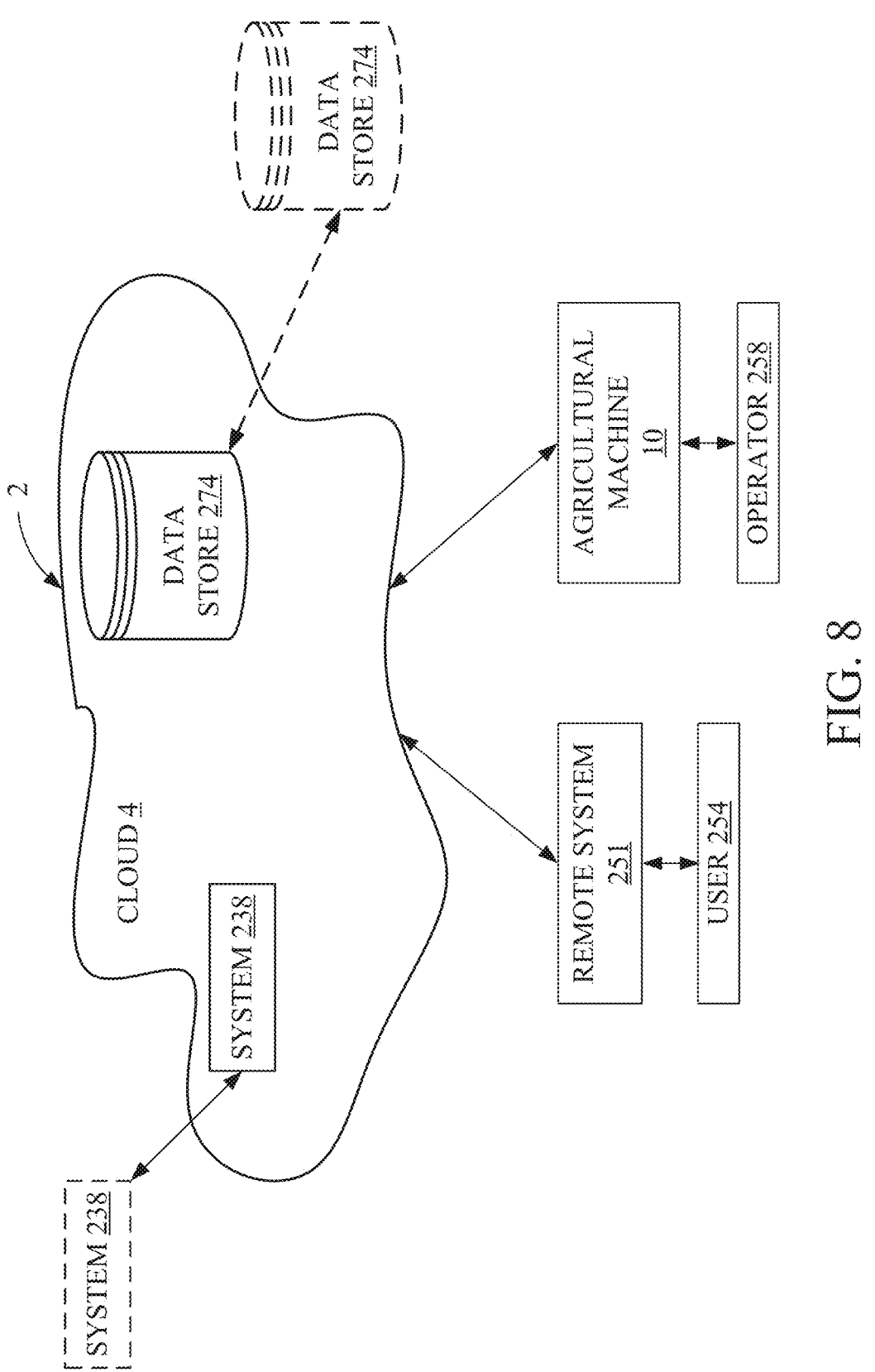
FIG. 8 is a diagrammatic view of an embodiment operating in a cloud architecture.

FIG. 8 is a block diagram of one example of the agricultural machine architecture, shown in FIG. 1, where agricultural machine 10 communicates with elements in a remote server architecture 2. In an example, remote server architecture 2 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in FIGS. 2 and/or 6 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 8, some items are similar to those shown in FIG. 2 and they are similarly numbered. FIG. 8 specifically shows that data store 272 and AI engine 274 can be located at a remote server location 4. Therefore, agricultural machine 10 accesses those systems through remote server location 4.

FIG. 8 also depicts another example of a remote server architecture. FIG. 8 shows that it is also contemplated that some elements of FIG. 2 are disposed at remote server location 4 while others are not. By way of example, data store 272 can be disposed at a location separate from location 4, and accessed through the remote server at location 4. In some examples, agricultural machine 10 operates autonomously or semi-autonomously without operator 258 on board. User 254 may monitor control operation of agricultural machine 10 using remote system 251, such as a cell phone or tablet computer, connected to agricultural machine 10 via cloud 4.

Regardless of where they are located, they can be accessed directly by agricultural machine 10, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the agricultural machine comes close to the fuel truck for fueling, the system automatically collects the information from the machine or transfers information to the machine using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the agricultural machine until the agricultural machine enters a covered location. The agricultural machine, itself, can then send and receive the information to/from the main network.

It will also be noted that the elements of FIGS. 2 and/or 6, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 9:
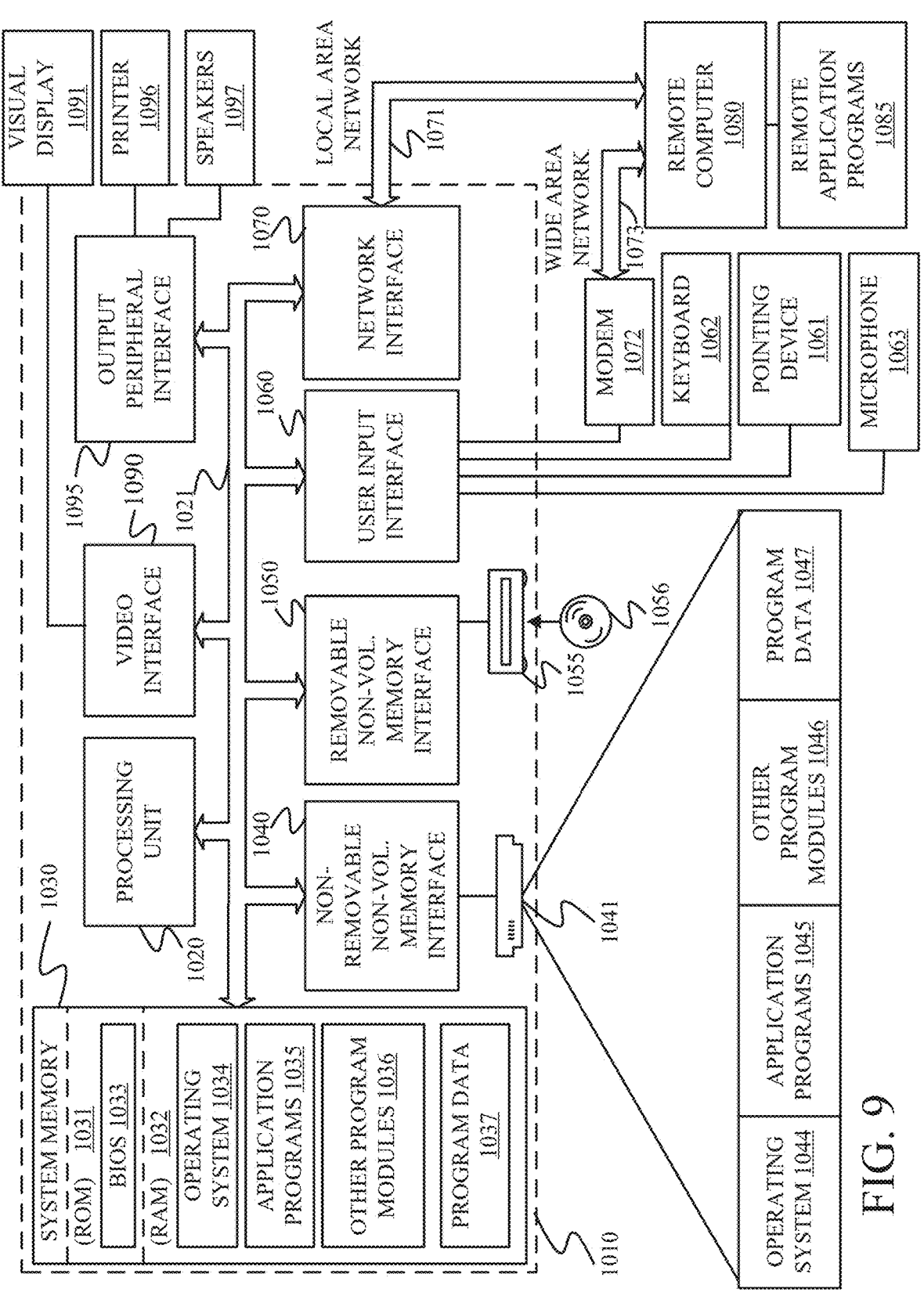
FIG. 9 is a block diagram showing one example of a computing environment that can be used in the architectures shown in the previous figures.

FIG. 9 is one example of a computing environment in which elements of FIGS. 2 and/or 6, or parts of it, (for example) can be deployed. With reference to FIG. 9, an example system for implementing some embodiments includes a computing device in the form of a computer 1010. Components of computer 1010 may include, but are not limited to, a processing unit 1020 (which can comprise processors or servers from previous FIGS.), a system memory 1030, and a system bus 1021 that couples various system components including the system memory to the processing unit 1020. The system bus 1021 may be any of several types of bus structures including a memory bus or memory controller, a peripheral bus, and a local bus using any of a variety of bus architectures. Memory and programs described with respect to FIG. 2 can be deployed in corresponding portions of FIG. 9.

Computer 1010 typically includes a variety of computer readable media. Computer readable media can be any available media that can be accessed by computer 1010 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1010. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 1030 includes computer storage media in the form of volatile and/or nonvolatile memory such as read only memory (ROM) 1031 and random access memory (RAM) 1032. A basic input/output system 1033 (BIOS), containing the basic routines that help to transfer information between elements within computer 1010, such as during start-up, is typically stored in ROM 1031. RAM 1032 typically contains data and/or program modules that are immediately accessible to and/or presently being operated on by processing unit 1020. By way of example, and not limitation, FIG. 20 illustrates operating system 1034, application programs 1035, other program modules 1036, and program data 1037.

The computer 1010 may also include other removable/non-removable volatile/nonvolatile computer storage media. By way of example only, FIG. 20 illustrates a hard disk drive 1041 that reads from or writes to non-removable, nonvolatile magnetic media, an optical disk drive 1055, and non-volatile optical disk 1056. The hard disk drive 1041 is typically connected to the system bus 1021 through a non-removable memory interface such as interface 1040, and optical disk drive 1055 is typically connected to the system bus 1021 by a removable memory interface, such as interface 1050.

Alternatively, or in addition, the functionality described herein can be performed, at least in part, by one or more hardware logic components. For example, and without limitation, illustrative types of hardware logic components that can be used include Field-programmable Gate Arrays (FP-GAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 9, provide storage of computer readable instructions, data structures, program modules and other data for the computer 1010. In FIG. 9, for example, hard disk drive 1041 is illustrated as storing operating system 1044, application programs 1045, other program modules 1046, and program data 1047. Note that these components can either be the same as or different from operating system 1034, application programs 1035, other program modules 1036, and program data 1037.

A user may enter commands and information into the computer 1010 through input devices such as a keyboard 1062, a microphone 1063, and a pointing device 1061, such as a mouse, trackball or touch pad. Other input devices (not shown) may include a joystick, game pad, satellite dish, scanner, or the like. These and other input devices are often connected to the processing unit 1020 through a user input interface 1060 that is coupled to the system bus, but may be connected by other interface and bus structures. A visual display 1091 or other type of display device is also connected to the system bus 1021 via an interface, such as a video interface 1090. In addition to the monitor, computers may also include other peripheral output devices such as speakers 1097 and printer 1096, which may be connected through an output peripheral interface 1095.

The computer 1010 is operated in a networked environment using logical connections (such as a local area network—LAN, or wide area network—WAN or a controller area network—CAN) to one or more remote computers, such as a remote computer 1080.

When used in a LAN networking environment, the computer 1010 is connected to the LAN 1071 through a network interface or adapter 1070. When used in a WAN networking environment, the computer 1010 typically includes a modem 1072 or other means for establishing communications over the WAN 1073, such as the Internet. In a networked environment, program modules may be stored in a remote memory storage device. FIG. 20 illustrates, for example, that remote application programs 1085 can reside on remote computer 1080.

It should also be noted that the different examples described herein can be combined in different ways. That is, parts of one or more examples can be combined with parts of one or more other examples. All of this is contemplated herein.

Example 1 is terahertz frequency-based sensing system for an agricultural harvester. The system comprising: a terahertz sensor mounted to the agricultural harvester, the terahertz sensor including at least one a terahertz source disposed to direct electromagnetic radiation toward a harvest material of the agricultural harvester; at least one terahertz detector disposed to detect the terahertz electromagnetic radiation after the terahertz electromagnetic radiation interacts with the harvest material; and a controller operably coupled to the at least one terahertz detector, the controller being configured to detect at least one harvest-related parameter based on a signal from the at least one terahertz detector and to perform an action based on the at least one detected parameter.

Example 2 is the terahertz frequency-based sensing system of any or all of the previous examples, wherein the agricultural harvester is a combine.

Example 3 is the terahertz frequency-based sensing system of any or all of the previous examples, wherein the terahertz sensor is mounted to a front portion of the agricultural harvester.

Example 4 is the terahertz frequency-based sensing system of any or all of the previous examples, wherein the terahertz sensor is mounted to a rear portion of the agricultural harvester.

Example 5 is the terahertz frequency-based sensing system of any or all of the previous examples, wherein the terahertz sensor is mounted to the agricultural harvester at a location along a clean grain stream.

Example 6 is the terahertz frequency-based sensing system of any or all of the previous examples, wherein the controller is configured to employ an artificial intelligence engine to relate the signal from the at least one detector to the at least one detected parameter.

Example 7 is the terahertz frequency-based sensing system of any or all of the previous examples, and further comprising at least one chemometric sensor disposed to sense a parameter of the harvest material, the at least one chemometric sensor being couple to the controller.

Example 8 is the terahertz frequency-based sensing system of any or all of the previous examples, wherein the controller is configured to detect contamination of the harvest material and wherein the action includes stopping a feeding system of the agricultural harvester.

Example 9 is the terahertz frequency-based sensing system of any or all of the previous examples, wherein the controller is configured to detect contamination of the harvest material and wherein the action includes notifying an operator of the agricultural harvester.

Example 10 is the terahertz frequency-based sensing system of any or all of the previous examples, wherein the controller is configured to detect contamination of the harvest material and wherein the action includes diverting the contaminated harvest material to a container within the agricultural harvester that is different from a crop container.

Example 11 is the terahertz frequency-based sensing system of any or all of the previous examples, wherein the controller is configured to detect contamination of the harvest material and wherein the action includes engaging a cutter of the agricultural harvester to break the contaminated material into smaller pieces.

Example 12 is the terahertz frequency-based sensing system of any or all of the previous examples, wherein the at least one terahertz detector is disposed to detect terahertz electromagnetic radiation reflected from the harvest material.

Example 13 is the terahertz frequency-based sensing system of any or all of the previous examples, wherein the at least one terahertz detector is disposed to detect terahertz electromagnetic radiation passing through the harvest material.

Example 14 is the terahertz frequency-based sensing system of any or all of the previous examples, wherein the at least one harvest-related parameter includes detection of non-ferrous foreign material.

Example 15 is the terahertz frequency-based sensing system of any or all of the previous examples, wherein the at least one harvest-related parameter includes detection of a genetically-modified organism.

Example 16 is the terahertz frequency-based sensing system of any or all of the previous examples, wherein the at least one harvest-related parameter includes detection of a pesticide.

Example 17 is the terahertz frequency-based sensing system of any or all of the previous examples, wherein the at least one harvest-related parameter includes detection of a biotoxin.

Example 18 is a method of detecting crop contamination during a harvest operation of an agricultural harvester. The method comprising: receiving, by a controller, a signal from a terahertz frequency-based detector mounted to the agricultural harvester; recalling, by the controller, appropriate terahertz characteristics from a database based on at least one of grain type, grain category, kernel type, kernel category, and moisture content; detecting a contaminant relative to the harvest operation based on the signal and the recalled terahertz characteristics; and selectively performing an action based on the detected contaminant.

Example 19 is the method of any or all of the previous examples, wherein the action is selected from the group consisting of: stopping a feeder system of the agricultural harvester, notifying an operator of the agricultural harvester, diverting contaminated material from a crop container of the agricultural harvester, and engaging a cutting system of the agricultural harvester to reduce particle size of non-ferrous foreign material.

Example 20 is a combine comprising: a main frame; a plurality of ground-engaging wheels supporting the main frame; a feederhouse mounted to a forward portion of the main frame; a header attached to the feederhouse, the header being configured to harvest a particular type of crop; a terahertz sensor mounted to the combine, the terahertz sensor including, at least one a terahertz source disposed to direct electromagnetic radiation toward a harvest material of the combine; at least one terahertz detector disposed to detect the terahertz electromagnetic radiation after the terahertz electromagnetic radiation interacts with the harvest material; and a controller operably coupled to the at least one terahertz detector, the controller being configured to detect at least one harvest-related parameter based on a signal from the at least one terahertz detector and to perform an action based on the at least one detected parameter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A terahertz frequency-based sensing system for an agricultural harvester, the system comprising:
a terahertz sensor mounted to the agricultural harvester, the terahertz sensor including,
at least one terahertz source disposed to direct terahertz electromagnetic radiation toward harvested material within the agricultural harvester during grain harvest by the agricultural harvester;
at least one terahertz detector disposed to detect the terahertz electromagnetic radiation after the terahertz electromagnetic radiation interacts with the harvested grain within the agricultural harvester; and
a controller operably coupled to the at least one terahertz detector, the controller being configured to:
receive a signal from the at least one terahertz detector:
access a characteristic database relating terahertz signal characteristics with harvested material constituents;
detect at least one harvest-related parameter based on the signal and the characteristic database; and
perform an action based on the at least one harvest-related parameter.

2. The system of claim 1, wherein the terahertz sensor is mounted to the agricultural harvester at a location along a clean grain stream.

3. The system of claim 1, wherein the controller is configured to employ an artificial intelligence engine to relate the signal from the at least one terahertz detector to the at least one harvest-related parameter.

4. The system of claim 1, and further comprising at least one chemical sensor coupled to the controller and disposed to sense a parameter of the harvested material.

5. The system of claim 1, wherein the controller is configured to detect contamination of the grain and wherein the action includes stopping a feeding system of the agricultural harvester.

6. The system of claim 1, wherein the controller is configured to detect contamination of the grain and wherein the action includes notifying an operator of the agricultural harvester.

7. The system of claim 1, wherein the controller is configured to detect contamination of the grain and wherein the action includes diverting the contaminated harvested grain to a container within the agricultural harvester that is different from a crop container.

8. The system of claim 1, wherein the controller is configured to detect contamination of the grain and wherein the action includes engaging a cutter of the agricultural harvester to break the contaminated harvested grain into smaller pieces.

9. The system of claim 1, wherein the at least one terahertz detector is disposed to detect terahertz electromagnetic radiation reflected from the harvested material.

10. The system of claim 1, wherein the at least one terahertz detector is disposed to detect terahertz electromagnetic radiation passing through the harvested material.

11. The system of claim 1, wherein the at least one harvest-related parameter includes detection of non-ferrous foreign material.

12. The system of claim 1, wherein the at least one harvest-related parameter includes detection of at least one of a genetically-modified organism, a pesticide, or a biotoxin.

13. The system of claim 1, wherein the harvested material comprises harvested grain, and the harvested material constituents comprise at least one of:
grain mass, moisture content, protein content, cellulose content, starch content, or oil content.

14. A method of detecting crop contamination during a harvest operation of an agricultural harvester, the method comprising:
receiving, by a controller, a signal from a terahertz frequency-based detector mounted to the agricultural harvester, the signal being indicative of terahertz electromagnetic radiation interacting with harvested material being harvested by the agricultural harvester while the harvested material is within the agricultural harvester;
recalling, by the controller, terahertz characteristics from a characteristic database that relates terahertz signal characteristics with harvested material constituents;
detecting a contaminant during the harvest operation based on the signal and the characteristic database; and
selectively performing an action based on the detected contaminant.

15. The method of claim 14, wherein the action is selected from the group consisting of: stopping a feeder system of the agricultural harvester, notifying an operator of the agricultural harvester, diverting contaminated material from a crop container of the agricultural harvester, and engaging a cutting system of the agricultural harvester to reduce particle size of non-ferrous foreign material.

16. The method of claim 14, wherein the terahertz characteristics comprise at least one of absorption, reflectance, and backscatter of a material selected from the group consisting of a non-ferrous metal, a plastic, a wood, a weed, a weed seed, a non-grain plant part, soil, ash, a fungi, a biotoxin, and a genetically modified organism.

17. A combine comprising:
a main frame;
a plurality of ground-engaging wheels supporting the main frame;
a feederhouse mounted to a forward portion of the main frame;
a header attached to the feederhouse, the header being configured to harvest a particular type of crop;
a terahertz sensor mounted to the combine, the terahertz sensor including:
at least one terahertz source disposed to direct terahertz electromagnetic radiation toward harvested material within the combine while the combine is harvesting the crop;
at least one terahertz detector disposed to detect the terahertz electromagnetic radiation after the terahertz electromagnetic radiation interacts with the harvested material inside the combine; and
a controller operably coupled to the at least one terahertz detector, the controller being configured to:
receive a signal from the at least one terahertz detector;
access a characteristic database relating terahertz signal characteristics with harvested material constituents;
detect at least one harvest-related parameter based on a signal from the at least one terahertz detector; and
perform an action based on the at least one harvest-related parameter.

18. The system of claim 1, wherein the harvested material comprises grain and non-material.

19. The system of claim 18, wherein the harvested material constituents comprise one or more of:

a non-ferrous metal, a plastic, a wood, a weed, a weed seed, a non-grain plant part, soil, ash, a fungi, a pesticide, a biotoxin, or a genetically modified organism.

20. The system of claim 18, wherein the harvested material constituents comprise one or more of:

a foreign object; or a contaminant.

\* \* \* \* \*